(12) United States Patent
Schlameuss et al.

(10) Patent No.: US 11,631,493 B2
(45) Date of Patent: Apr. 18, 2023

(54) SYSTEMS AND METHODS FOR MANAGING BUILDING WELLNESS

(71) Applicant: View Operating Corporation, Milpitas, CA (US)

(72) Inventors: Eric Schlameuss, Stamford, CT (US); Michael Aisner, New Rochelle, NY (US); Paul Rode, Tarrytown, NY (US); Greg Zimerman, Brooklyn, NY (US); Cory Clarke, Yonkers, NY (US); Scott Rechler, Old Brookville, NY (US); Francis Pusinelli, Hicksville, NY (US)

(73) Assignee: View Operating Corporation, Milpitas, CA (US)

( * ) Notice: Subject to any disclaimer, the term of this patent is extended or adjusted under 35 U.S.C. 154(b) by 0 days.

(21) Appl. No.: 17/328,346

(22) Filed: May 24, 2021

(65) Prior Publication Data
US 2021/0375440 A1 Dec. 2, 2021

Related U.S. Application Data

(60) Provisional application No. 63/030,507, filed on May 27, 2020.

(51) Int. Cl.
*G16H 40/20* (2018.01)
*G16H 10/60* (2018.01)
(Continued)

(52) U.S. Cl.
CPC ............ *G16H 40/20* (2018.01); *G01N 33/18* (2013.01); *G05B 15/02* (2013.01);
(Continued)

(58) Field of Classification Search
CPC ........ G16H 40/20; G16H 50/30; G16H 15/00; G16H 10/60; G06Q 10/0635;
(Continued)

(56) References Cited

U.S. PATENT DOCUMENTS

| 4,129,861 A | 12/1978 | Giglia |
| 4,148,015 A | 4/1979 | Sekiya et al. |

(Continued)

FOREIGN PATENT DOCUMENTS

| AU | 2015101660 A4 | 12/2015 |
| CN | 1161092 A | 10/1997 |

(Continued)

OTHER PUBLICATIONS

"The Office of the Future Starts with Innerspace," InnerSpace Smart Solutions: Corporate Real Estate, 13 pp., URL:https://innerspace.io/corporate-office-use-cases.

(Continued)

*Primary Examiner* — Eliza A Lam
(74) *Attorney, Agent, or Firm* — Weaver Austin Villeneuve & Sampson LLP; Ryan Otis

(57) ABSTRACT

A system and a computer-implemented method of managing building wellness. The method may include the steps of: obtaining wellness parameters for a building (e.g., an office building) having an occupant(s); processing the wellness parameters to determine a current wellness index for the building; and, based on the current wellness index, sending a message regarding the current wellness index to a recipient(s) (e.g., a building occupant), displaying the current wellness index for a user(s), and/or identifying a remediation action(s) to improve the current wellness index.

23 Claims, 2 Drawing Sheets

(51) Int. Cl.

| | | |
|---|---|---|
| *G06Q 10/06* | (2012.01) | |
| *G06Q 10/10* | (2012.01) | |
| *G16H 50/30* | (2018.01) | |
| *G05B 15/02* | (2006.01) | |
| *G01N 33/18* | (2006.01) | |
| *G16H 15/00* | (2018.01) | |
| *G06Q 50/26* | (2012.01) | |
| *G06Q 50/16* | (2012.01) | |
| *G06Q 10/0635* | (2023.01) | |
| *G06Q 10/105* | (2023.01) | |

(52) U.S. Cl.
CPC ....... *G06Q 10/0635* (2013.01); *G06Q 10/105* (2013.01); *G16H 10/60* (2018.01); *G16H 15/00* (2018.01); *G16H 50/30* (2018.01); *G06Q 50/163* (2013.01); *G06Q 50/26* (2013.01)

(58) Field of Classification Search
CPC .... G06Q 10/105; G06Q 50/163; G06Q 50/26; G01N 33/18; G05B 15/02
See application file for complete search history.

(56) References Cited

U.S. PATENT DOCUMENTS

| | | |
|---|---|---|
| 4,340,813 A | 7/1982 | Sauer |
| 4,491,727 A | 1/1985 | Appelbaum et al. |
| 4,553,085 A | 11/1985 | Canzano |
| 4,864,314 A | 9/1989 | Bond |
| 4,874,903 A | 10/1989 | Clarke |
| 4,923,289 A | 5/1990 | Demiryont |
| 4,932,755 A | 6/1990 | Holdridge et al. |
| 5,124,833 A | 6/1992 | Barton et al. |
| 5,139,850 A | 8/1992 | Clarke et al. |
| 5,147,694 A | 9/1992 | Clarke |
| 5,170,108 A | 12/1992 | Peterson et al. |
| 5,204,778 A | 4/1993 | Bechtel |
| 5,220,317 A | 6/1993 | Lynam et al. |
| 5,242,313 A | 9/1993 | Logerot et al. |
| 5,290,986 A | 3/1994 | Colon et al. |
| 5,353,148 A | 10/1994 | Eid et al. |
| 5,365,365 A | 11/1994 | Ripoche et al. |
| 5,379,146 A | 1/1995 | Defendini |
| 5,384,578 A | 1/1995 | Lynam et al. |
| 5,384,653 A | 1/1995 | Benson et al. |
| 5,390,045 A | 2/1995 | Bernard, Jr. |
| 5,402,144 A | 3/1995 | Ripoche |
| 5,416,617 A | 5/1995 | Loiseaux et al. |
| 5,440,317 A | 8/1995 | Jalloul et al. |
| 5,451,822 A | 9/1995 | Bechtel et al. |
| 5,477,152 A | 12/1995 | Hayhurst |
| 5,579,149 A | 11/1996 | Moret et al. |
| 5,598,000 A | 1/1997 | Popat |
| 5,621,526 A | 4/1997 | Kuze |
| 5,673,028 A | 9/1997 | Levy |
| 5,694,144 A | 12/1997 | Lefrou et al. |
| 5,729,824 A | 3/1998 | O'Neill et al. |
| 5,764,402 A | 6/1998 | Thomas et al. |
| 5,822,107 A | 10/1998 | Lefrou et al. |
| 5,900,720 A | 5/1999 | Kallman et al. |
| 5,956,012 A | 9/1999 | Turnbull et al. |
| 5,959,586 A | 9/1999 | Benham et al. |
| 5,973,818 A | 10/1999 | Sjursen et al. |
| 5,973,819 A | 10/1999 | Pletcher et al. |
| 5,978,126 A | 11/1999 | Sjursen |
| 6,032,020 A | 2/2000 | Cook et al. |
| 6,039,390 A | 3/2000 | Agrawal et al. |
| 6,039,850 A | 3/2000 | Schulz |
| 6,055,089 A | 4/2000 | Schulz et al. |
| 6,066,801 A | 5/2000 | Kodaira et al. |
| 6,084,700 A | 7/2000 | Knapp et al. |
| 6,084,758 A | 7/2000 | Clarey et al. |
| 6,104,513 A | 8/2000 | Bloom |
| 6,128,471 A | 10/2000 | Quelch et al. |
| 6,130,448 A | 10/2000 | Bauer et al. |
| 6,130,772 A | 10/2000 | Cava |
| 6,222,177 B1 | 4/2001 | Bechtel et al. |
| 6,232,557 B1 | 5/2001 | Lounsbury et al. |
| 6,262,831 B1 | 7/2001 | Bauer et al. |
| 6,344,748 B1 | 2/2002 | Gannon |
| 6,386,713 B1 | 5/2002 | Turnbull et al. |
| 6,407,468 B1 | 6/2002 | LeVesque et al. |
| 6,407,847 B1 | 6/2002 | Poll et al. |
| 6,417,500 B1 | 7/2002 | Wood |
| 6,449,082 B1 | 9/2002 | Agrawal et al. |
| 6,456,239 B1 | 9/2002 | Werb et al. |
| 6,471,360 B2 | 10/2002 | Rukavina et al. |
| 6,535,126 B2 | 3/2003 | Lin et al. |
| 6,567,708 B1 | 5/2003 | Bechtel et al. |
| 6,588,250 B2 | 7/2003 | Schell |
| 6,614,577 B1 | 9/2003 | Yu et al. |
| 6,703,981 B2 | 3/2004 | Meitzler et al. |
| 6,707,590 B1 | 3/2004 | Bartsch |
| 6,795,226 B2 | 9/2004 | Agrawal et al. |
| 6,809,692 B2 | 10/2004 | Puente Baliarda et al. |
| 6,829,511 B2 | 12/2004 | Bechtel et al. |
| 6,848,933 B1 | 2/2005 | Delaney, III et al. |
| 6,856,444 B2 | 2/2005 | Ingalls et al. |
| 6,897,936 B1 | 5/2005 | Li et al. |
| 6,940,627 B2 | 9/2005 | Freeman et al. |
| 6,965,813 B2 | 11/2005 | Granqvist et al. |
| 7,031,727 B2 | 4/2006 | Baskin |
| 7,085,609 B2 | 8/2006 | Bechtel et al. |
| 7,111,952 B2 | 9/2006 | Veskovic |
| 7,133,181 B2 | 11/2006 | Greer |
| 7,214,346 B2 | 5/2007 | Harper et al. |
| 7,215,318 B2 | 5/2007 | Turnbull et al. |
| 7,277,215 B2 | 10/2007 | Greer |
| 7,304,787 B2 | 12/2007 | Whitesides et al. |
| 7,310,355 B1 | 12/2007 | Krein et al. |
| 7,382,636 B2 | 6/2008 | Baarman et al. |
| 7,417,397 B2 | 8/2008 | Berman et al. |
| 7,480,692 B2 | 1/2009 | Atsmon et al. |
| 7,542,809 B2 | 6/2009 | Bechtel et al. |
| 7,548,833 B2 | 6/2009 | Ahmed |
| 7,554,437 B2 | 6/2009 | Axelsen |
| 7,567,183 B2 | 7/2009 | Schwenke |
| 7,588,067 B2 | 9/2009 | Veskovic |
| 7,610,910 B2 | 11/2009 | Ahmed |
| 7,629,400 B2 | 12/2009 | Hyman |
| 7,672,104 B2 | 3/2010 | Reynolds et al. |
| 7,684,105 B2 | 3/2010 | Lamontagne et al. |
| 7,722,948 B2 | 5/2010 | Dixon et al. |
| 7,722,966 B1 | 5/2010 | Lee et al. |
| 7,797,367 B1 | 9/2010 | Gelvin et al. |
| 7,800,812 B2 | 9/2010 | Moskowitz |
| 7,817,326 B1 | 10/2010 | Rennig et al. |
| 7,822,490 B2 | 10/2010 | Bechtel et al. |
| 7,873,490 B2 | 1/2011 | MacDonald |
| 7,908,155 B2 | 3/2011 | Fuerst et al. |
| 7,911,348 B2 | 3/2011 | Rodgers |
| 7,941,245 B1 | 5/2011 | Popat |
| 7,950,827 B2 | 5/2011 | Veskovic |
| 7,963,675 B2 | 6/2011 | Veskovic |
| 7,972,021 B2 | 7/2011 | Scherer |
| 7,990,603 B2 | 8/2011 | Ash et al. |
| 8,004,739 B2 | 8/2011 | Letocart |
| 8,018,644 B2 | 9/2011 | Gustavsson et al. |
| 8,022,977 B2 | 9/2011 | Kanade et al. |
| 8,086,433 B2 | 12/2011 | Lee et al. |
| 8,102,586 B2 | 1/2012 | Albahri |
| 8,140,276 B2 | 3/2012 | Walters et al. |
| 8,149,756 B2 | 4/2012 | Hottinen |
| 8,213,074 B1 | 7/2012 | Shrivastava et al. |
| 8,249,731 B2 | 8/2012 | Tran et al. |
| 8,254,013 B2 | 8/2012 | Mehtani et al. |
| 8,292,228 B2 | 10/2012 | Mitchell et al. |
| 8,296,287 B1 | 10/2012 | Cappiello et al. |
| 8,401,873 B2 | 3/2013 | Brown et al. |
| 8,446,275 B2 | 5/2013 | Utter, II |
| 8,456,729 B2 | 6/2013 | Brown et al. |
| 8,547,624 B2 | 10/2013 | Ash et al. |

(56) References Cited

U.S. PATENT DOCUMENTS

| | | |
|---|---|---|
| 8,614,848 B2 | 12/2013 | Ueda et al. |
| 8,634,764 B2 | 1/2014 | Cruz et al. |
| 8,647,270 B2 | 2/2014 | LeBoeuf et al. |
| 8,705,162 B2 | 4/2014 | Brown et al. |
| 8,711,465 B2 | 4/2014 | Bhatnagar et al. |
| 8,723,467 B2 | 5/2014 | Berman et al. |
| 8,780,432 B1 | 7/2014 | Nguyen |
| 8,800,221 B1 | 8/2014 | Header |
| 8,836,263 B2 | 9/2014 | Berman et al. |
| 8,843,238 B2 | 9/2014 | Wenzel et al. |
| 8,862,448 B2 | 10/2014 | Holmes et al. |
| 8,864,321 B2 | 10/2014 | Mehtani et al. |
| 8,902,486 B1 | 12/2014 | Chandrasekhar |
| 8,924,076 B2 | 12/2014 | Boote et al. |
| 8,927,069 B1 | 1/2015 | Estinto et al. |
| 8,975,789 B2 | 3/2015 | Snyker et al. |
| 8,976,440 B2 | 3/2015 | Berland et al. |
| 8,994,540 B2 | 3/2015 | Fadell et al. |
| 9,016,630 B2 | 4/2015 | Mitchell et al. |
| 9,030,725 B2 | 5/2015 | Pradhan et al. |
| 9,081,246 B2 | 7/2015 | Rozbicki |
| 9,081,247 B1 | 7/2015 | Pradhan et al. |
| 9,121,837 B2 | 9/2015 | Chan et al. |
| 9,128,346 B2 | 9/2015 | Shrivastava et al. |
| 9,170,008 B2 | 10/2015 | Reul et al. |
| 9,225,286 B1 | 12/2015 | Tweedie |
| 9,250,494 B2 | 2/2016 | Podbelski et al. |
| 9,300,581 B1 | 3/2016 | Hui et al. |
| 9,442,338 B2 | 9/2016 | Uhm et al. |
| 9,442,341 B2 | 9/2016 | Shrivastava et al. |
| 9,454,055 B2 | 9/2016 | Brown et al. |
| 9,470,947 B2 | 10/2016 | Nagel et al. |
| 9,494,055 B2 | 11/2016 | Rusche |
| 9,551,913 B2 | 1/2017 | Kim et al. |
| 9,648,888 B2 | 5/2017 | Davidson |
| 9,664,976 B2 | 5/2017 | Rozbicki |
| 9,677,327 B1 | 6/2017 | Nagel et al. |
| 9,690,174 B2 | 6/2017 | Wang |
| 9,709,869 B2 | 7/2017 | Baumann et al. |
| 9,715,242 B2 * | 7/2017 | Pillai .................. H04L 12/2827 |
| 9,740,074 B2 | 8/2017 | Agrawal et al. |
| 9,778,533 B2 | 10/2017 | Bertolini |
| 9,883,209 B2 | 1/2018 | Ricci |
| 9,898,912 B1 | 2/2018 | Jordan, II et al. |
| 9,938,765 B2 | 4/2018 | Berman et al. |
| 9,946,138 B2 | 4/2018 | Shrivastava et al. |
| 9,965,865 B1 | 5/2018 | Agrawal et al. |
| 10,001,691 B2 | 6/2018 | Shrivastava et al. |
| 10,137,764 B2 | 11/2018 | Driscoll et al. |
| 10,153,845 B2 | 12/2018 | Ashrafi |
| 10,156,852 B2 | 12/2018 | Bakhishev et al. |
| 10,178,638 B1 | 1/2019 | Stamatakis et al. |
| 10,253,558 B2 | 4/2019 | Vigano et al. |
| 10,254,618 B2 | 4/2019 | Parker |
| 10,268,098 B2 | 4/2019 | Shrivastava et al. |
| 10,286,839 B1 | 5/2019 | Mazuir et al. |
| 10,288,971 B2 | 5/2019 | Phillips et al. |
| 10,289,094 B2 | 5/2019 | Ashdown et al. |
| 10,299,101 B1 | 5/2019 | Lim et al. |
| 10,303,035 B2 | 5/2019 | Brown et al. |
| 10,322,680 B2 | 6/2019 | Terashima et al. |
| 10,329,839 B2 | 6/2019 | Fasi et al. |
| 10,365,532 B2 | 7/2019 | Vigano et al. |
| 10,372,007 B1 | 8/2019 | Nagel et al. |
| 10,387,221 B2 | 8/2019 | Shrivastava et al. |
| 10,409,652 B2 | 9/2019 | Shrivastava et al. |
| 10,481,459 B2 | 11/2019 | Shrivastava et al. |
| 10,488,837 B2 | 11/2019 | Cirino |
| 10,495,939 B2 | 12/2019 | Brown et al. |
| 10,502,442 B2 | 12/2019 | Guan et al. |
| 10,506,406 B2 | 12/2019 | Grohman |
| 10,514,963 B2 | 12/2019 | Shrivastava et al. |
| 10,673,121 B2 | 6/2020 | Hughes et al. |
| 10,704,322 B2 | 7/2020 | Vigano et al. |
| 10,720,766 B2 | 7/2020 | Krammer et al. |
| 10,724,867 B1 | 7/2020 | Waful et al. |
| 10,746,761 B2 | 8/2020 | Rayman et al. |
| 10,747,082 B2 | 8/2020 | Shrivastava et al. |
| 10,768,503 B1 | 9/2020 | Nagel et al. |
| 10,768,582 B2 | 9/2020 | Shrivastava et al. |
| 10,797,373 B2 | 10/2020 | Hughes et al. |
| 10,809,587 B2 | 10/2020 | Brown et al. |
| 10,809,589 B2 | 10/2020 | Brown |
| 10,859,887 B2 | 12/2020 | Vigano et al. |
| 10,859,983 B2 | 12/2020 | Shrivastava et al. |
| 10,867,266 B1 | 12/2020 | Carlin et al. |
| 10,917,259 B1 | 2/2021 | Chein et al. |
| 10,921,465 B2 | 2/2021 | Yoshioka et al. |
| 10,921,675 B2 | 2/2021 | Barnum et al. |
| 10,923,226 B2 | 2/2021 | Macary et al. |
| 10,949,267 B2 | 3/2021 | Shrivastava et al. |
| 10,954,677 B1 | 3/2021 | Scanlin |
| 10,956,231 B2 | 3/2021 | Shrivastava et al. |
| 10,982,487 B2 | 4/2021 | Ramirez |
| 10,989,977 B2 | 4/2021 | Shrivastava et al. |
| 11,016,357 B2 | 5/2021 | Brown et al. |
| 11,054,711 B2 | 7/2021 | Shrivastava et al. |
| 11,054,792 B2 | 7/2021 | Shrivastava et al. |
| 11,073,800 B2 | 7/2021 | Shrivastava et al. |
| 11,114,742 B2 | 9/2021 | Shrivastava et al. |
| 11,150,616 B2 | 10/2021 | Shrivastava et al. |
| 11,168,910 B2 | 11/2021 | Alcala Perez |
| 11,175,178 B2 | 11/2021 | Brown et al. |
| 11,205,926 B2 | 12/2021 | Shrivastava et al. |
| 11,237,449 B2 | 2/2022 | Brown et al. |
| 11,294,254 B2 | 4/2022 | Patterson et al. |
| 11,300,848 B2 | 4/2022 | Brown et al. |
| 11,320,713 B2 | 5/2022 | Tinianov et al. |
| 11,342,791 B2 | 5/2022 | Rozbicki et al. |
| 11,384,596 B2 | 7/2022 | Shrivastava et al. |
| 11,436,061 B2 | 9/2022 | Shrivastava et al. |
| 11,445,025 B2 | 9/2022 | Shrivastava et al. |
| 11,462,814 B2 | 10/2022 | Hughes et al. |
| 2002/0027504 A1 | 3/2002 | Davis et al. |
| 2002/0072868 A1 | 6/2002 | Bartone et al. |
| 2002/0075472 A1 | 6/2002 | Holton |
| 2002/0109634 A1 | 8/2002 | Aisenbrey |
| 2002/0140611 A1 | 10/2002 | Ligander et al. |
| 2002/0149829 A1 | 10/2002 | Mochizuka et al. |
| 2002/0152298 A1 | 10/2002 | Kikta et al. |
| 2003/0007462 A1 | 1/2003 | Makinen et al. |
| 2003/0034926 A1 | 2/2003 | Veerasamy |
| 2003/0039257 A1 | 2/2003 | Manis et al. |
| 2003/0052854 A1 | 3/2003 | Juang |
| 2003/0072144 A1 | 4/2003 | Malkowski, Jr. et al. |
| 2003/0098791 A1 | 5/2003 | Carlson et al. |
| 2003/0138812 A1 | 7/2003 | Downs |
| 2003/0163351 A1 * | 8/2003 | Brown .................. G16H 40/67 705/2 |
| 2003/0169574 A1 | 9/2003 | Maruyama et al. |
| 2003/0191546 A1 | 10/2003 | Bechtel et al. |
| 2003/0210449 A1 | 11/2003 | Ingalls et al. |
| 2003/0210450 A1 | 11/2003 | Yu et al. |
| 2003/0227663 A1 | 12/2003 | Agrawal et al. |
| 2003/0227664 A1 | 12/2003 | Agrawal et al. |
| 2003/0232181 A1 | 12/2003 | Simpson et al. |
| 2004/0001056 A1 | 1/2004 | Atherton et al. |
| 2004/0135989 A1 | 7/2004 | Klebe |
| 2004/0148057 A1 | 7/2004 | Breed et al. |
| 2004/0160322 A1 | 8/2004 | Stilp |
| 2004/0160324 A1 | 8/2004 | Stilp |
| 2004/0160657 A1 | 8/2004 | Tonar et al. |
| 2004/0196179 A1 | 10/2004 | Turnbull |
| 2004/0215520 A1 | 10/2004 | Butler et al. |
| 2005/0002662 A1 | 1/2005 | Arpa et al. |
| 2005/0063036 A1 | 3/2005 | Bechtel et al. |
| 2005/0082639 A1 | 4/2005 | Kikuta et al. |
| 2005/0117193 A1 | 6/2005 | Poll et al. |
| 2005/0157675 A1 | 7/2005 | Feder et al. |
| 2005/0200934 A1 | 9/2005 | Callahan et al. |
| 2005/0213992 A1 | 9/2005 | Piehler |
| 2005/0225830 A1 | 10/2005 | Huang et al. |
| 2005/0254442 A1 | 11/2005 | Proctor et al. |
| 2005/0260983 A1 | 11/2005 | DiPiazza |

(56) References Cited

U.S. PATENT DOCUMENTS

| | | |
|---|---|---|
| 2005/0268629 A1 | 12/2005 | Ahmed |
| 2005/0270620 A1 | 12/2005 | Bauer et al. |
| 2005/0270621 A1 | 12/2005 | Bauer et al. |
| 2005/0278047 A1 | 12/2005 | Ahmed |
| 2006/0018000 A1 | 1/2006 | Greer |
| 2006/0033663 A1 | 2/2006 | Saint Clair et al. |
| 2006/0074494 A1 | 4/2006 | McFarland |
| 2006/0107616 A1 | 5/2006 | Ratti et al. |
| 2006/0145833 A1 | 7/2006 | Brandt et al. |
| 2006/0158805 A1 | 7/2006 | Malvino |
| 2006/0170376 A1 | 8/2006 | Piepgras et al. |
| 2006/0174333 A1 | 8/2006 | Thomas et al. |
| 2006/0187608 A1 | 8/2006 | Stark |
| 2006/0202648 A1 | 9/2006 | O'Higgins et al. |
| 2006/0207730 A1 | 9/2006 | Berman et al. |
| 2006/0209007 A1 | 9/2006 | Pyo et al. |
| 2006/0245024 A1 | 11/2006 | Greer |
| 2006/0270440 A1 | 11/2006 | Shearer et al. |
| 2006/0279527 A1 | 12/2006 | Zehner et al. |
| 2007/0002007 A1 | 1/2007 | Tam |
| 2007/0042819 A1 | 2/2007 | Li et al. |
| 2007/0053053 A1 | 3/2007 | Moskowitz |
| 2007/0067048 A1 | 3/2007 | Bechtel et al. |
| 2007/0109989 A1 | 5/2007 | Nakagawa et al. |
| 2007/0126637 A1 | 6/2007 | Habib et al. |
| 2007/0135971 A1 | 6/2007 | Andarawis et al. |
| 2007/0162233 A1 | 7/2007 | Schwenke |
| 2007/0188841 A1 | 8/2007 | Moeller et al. |
| 2007/0191074 A1 | 8/2007 | Harrist et al. |
| 2007/0222542 A1 | 9/2007 | Joannopoulos et al. |
| 2007/0285759 A1 | 12/2007 | Ash et al. |
| 2007/0292606 A1 | 12/2007 | Demiryont |
| 2008/0018979 A1 | 1/2008 | Mahe et al. |
| 2008/0019068 A1 | 1/2008 | Reynolds et al. |
| 2008/0042012 A1 | 2/2008 | Callahan et al. |
| 2008/0043316 A2 | 2/2008 | Moskowitz |
| 2008/0048101 A1 | 2/2008 | Romig et al. |
| 2008/0147847 A1 | 6/2008 | Pitkow et al. |
| 2008/0172312 A1 | 7/2008 | Synesiou et al. |
| 2008/0177919 A1 | 7/2008 | Miyazawa |
| 2008/0182506 A1 | 7/2008 | Jackson et al. |
| 2008/0186562 A2 | 8/2008 | Moskowitz |
| 2008/0211682 A1 | 9/2008 | Hyland et al. |
| 2008/0230653 A1 | 9/2008 | Mitchell et al. |
| 2008/0234893 A1 | 9/2008 | Mitchell et al. |
| 2008/0238706 A1 | 10/2008 | Kenwright |
| 2008/0239451 A1 | 10/2008 | Mitchell et al. |
| 2008/0277486 A1 | 11/2008 | Seem et al. |
| 2009/0013317 A1 | 1/2009 | Abfalter et al. |
| 2009/0027759 A1 | 1/2009 | Albahri |
| 2009/0047900 A1 | 2/2009 | Cruz et al. |
| 2009/0054054 A1 | 2/2009 | Shao et al. |
| 2009/0066157 A1 | 3/2009 | Tarng et al. |
| 2009/0139052 A1 | 6/2009 | Boenisch |
| 2009/0143141 A1 | 6/2009 | Wells et al. |
| 2009/0179923 A1 | 7/2009 | Amundson et al. |
| 2009/0210252 A1* | 8/2009 | Silver .................. G16H 40/20 705/3 |
| 2009/0222223 A1 | 9/2009 | Walters et al. |
| 2009/0224980 A1 | 9/2009 | Cruz et al. |
| 2009/0243732 A1 | 10/2009 | Tarng et al. |
| 2009/0243802 A1 | 10/2009 | Wolf et al. |
| 2009/0271042 A1 | 10/2009 | Voysey |
| 2009/0284220 A1 | 11/2009 | Toncich et al. |
| 2009/0319807 A1 | 12/2009 | Chasen et al. |
| 2009/0322347 A1 | 12/2009 | Hashimshony et al. |
| 2009/0323160 A1 | 12/2009 | Egerton et al. |
| 2010/0027694 A1 | 2/2010 | Touboul et al. |
| 2010/0039410 A1 | 2/2010 | Becker et al. |
| 2010/0052718 A1 | 3/2010 | Baker et al. |
| 2010/0066484 A1 | 3/2010 | Hanwright et al. |
| 2010/0076615 A1 | 3/2010 | Daniel et al. |
| 2010/0082081 A1 | 4/2010 | Niessen et al. |
| 2010/0165436 A1 | 7/2010 | Voss et al. |
| 2010/0171667 A1 | 7/2010 | Knudsen |
| 2010/0172009 A1 | 7/2010 | Matthews |
| 2010/0172010 A1 | 7/2010 | Gustavsson et al. |
| 2010/0188057 A1 | 7/2010 | Tarng |
| 2010/0210233 A1 | 8/2010 | Cook et al. |
| 2010/0228854 A1 | 9/2010 | Morrison et al. |
| 2010/0235206 A1 | 9/2010 | Miller et al. |
| 2010/0243427 A1 | 9/2010 | Kozlowski et al. |
| 2010/0245972 A1 | 9/2010 | Wright |
| 2010/0245973 A1 | 9/2010 | Wang et al. |
| 2010/0274366 A1 | 10/2010 | Fata et al. |
| 2010/0286937 A1 | 11/2010 | Hedley et al. |
| 2010/0302624 A1 | 12/2010 | Moskowitz |
| 2010/0315693 A1 | 12/2010 | Lam et al. |
| 2011/0031821 A1 | 2/2011 | Greene et al. |
| 2011/0046810 A1 | 2/2011 | Bechtel et al. |
| 2011/0050756 A1 | 3/2011 | Cassidy et al. |
| 2011/0063708 A1 | 3/2011 | Letocart |
| 2011/0071685 A1 | 3/2011 | Huneycutt et al. |
| 2011/0074342 A1 | 3/2011 | MacLaughlin |
| 2011/0080630 A1 | 4/2011 | Valentin et al. |
| 2011/0097081 A1 | 4/2011 | Gupta et al. |
| 2011/0124313 A1 | 5/2011 | Jones |
| 2011/0148218 A1 | 6/2011 | Rozbicki |
| 2011/0159821 A1 | 6/2011 | Park |
| 2011/0164304 A1 | 7/2011 | Brown et al. |
| 2011/0164317 A1 | 7/2011 | Vergohl et al. |
| 2011/0167617 A1 | 7/2011 | Letocart |
| 2011/0170170 A1 | 7/2011 | Boote |
| 2011/0235152 A1 | 9/2011 | Letocart |
| 2011/0248901 A1 | 10/2011 | Alexopoulos et al. |
| 2011/0249313 A1 | 10/2011 | Letocart |
| 2011/0255142 A1 | 10/2011 | Ash et al. |
| 2011/0260856 A1 | 10/2011 | Rossmann et al. |
| 2011/0261429 A1 | 10/2011 | Sbar et al. |
| 2011/0266137 A1 | 11/2011 | Wang et al. |
| 2011/0266138 A1 | 11/2011 | Wang et al. |
| 2011/0266419 A1 | 11/2011 | Jones et al. |
| 2011/0267674 A1 | 11/2011 | Wang et al. |
| 2011/0267675 A1 | 11/2011 | Wang et al. |
| 2011/0292488 A1 | 12/2011 | McCarthy et al. |
| 2011/0304898 A1 | 12/2011 | Letocart |
| 2011/0304899 A1 | 12/2011 | Kwak et al. |
| 2011/0308318 A1 | 12/2011 | Magnussen |
| 2011/0310519 A1 | 12/2011 | Baba et al. |
| 2012/0007507 A1 | 1/2012 | Niemann et al. |
| 2012/0026573 A1 | 2/2012 | Collins et al. |
| 2012/0032855 A1 | 2/2012 | Reede et al. |
| 2012/0033287 A1 | 2/2012 | Friedman et al. |
| 2012/0039526 A1 | 2/2012 | Garaas et al. |
| 2012/0062975 A1 | 3/2012 | Mehtani et al. |
| 2012/0086363 A1 | 4/2012 | Golding et al. |
| 2012/0112883 A1 | 5/2012 | Wallace et al. |
| 2012/0133213 A1 | 5/2012 | Borke et al. |
| 2012/0133315 A1 | 5/2012 | Berman et al. |
| 2012/0140492 A1 | 6/2012 | Alvarez |
| 2012/0143516 A1 | 6/2012 | Mezic et al. |
| 2012/0154241 A1 | 6/2012 | Tatarnikov et al. |
| 2012/0182593 A1 | 7/2012 | Collins et al. |
| 2012/0188627 A1 | 7/2012 | Chen et al. |
| 2012/0190386 A1 | 7/2012 | Anderson |
| 2012/0194895 A1 | 8/2012 | Podbelski et al. |
| 2012/0200908 A1 | 8/2012 | Bergh et al. |
| 2012/0215874 A1 | 8/2012 | Sequeira et al. |
| 2012/0217346 A1 | 8/2012 | Eberle et al. |
| 2012/0229275 A1 | 9/2012 | Mattern |
| 2012/0235493 A1 | 9/2012 | Kiuchi et al. |
| 2012/0236386 A1 | 9/2012 | Mehtani et al. |
| 2012/0239209 A1 | 9/2012 | Brown et al. |
| 2012/0259583 A1 | 10/2012 | Noboa et al. |
| 2012/0268803 A1 | 10/2012 | Greer et al. |
| 2012/0275008 A1 | 11/2012 | Pradhan et al. |
| 2012/0287017 A1 | 11/2012 | Parsche |
| 2012/0293855 A1 | 11/2012 | Shrivastava et al. |
| 2012/0296610 A1 | 11/2012 | Hailemariam et al. |
| 2012/0300516 A1 | 11/2012 | Chen et al. |
| 2012/0323382 A1 | 12/2012 | Kamel et al. |
| 2012/0328849 A1 | 12/2012 | Neill et al. |
| 2013/0013921 A1 | 1/2013 | Bhathena et al. |
| 2013/0024029 A1 | 1/2013 | Tran et al. |

(56) References Cited

U.S. PATENT DOCUMENTS

| | | |
|---|---|---|
| 2013/0038218 A1 | 2/2013 | Xu et al. |
| 2013/0043347 A1 | 2/2013 | Mitchell et al. |
| 2013/0054033 A1 | 2/2013 | Casilli |
| 2013/0057937 A1 | 3/2013 | Berman et al. |
| 2013/0060357 A1 | 3/2013 | Li et al. |
| 2013/0073681 A1 | 3/2013 | Jiang et al. |
| 2013/0085614 A1 | 4/2013 | Wenzel et al. |
| 2013/0085615 A1 | 4/2013 | Barker |
| 2013/0085616 A1 | 4/2013 | Wenzel |
| 2013/0088331 A1 | 4/2013 | Cho et al. |
| 2013/0130227 A1 | 5/2013 | Peltz et al. |
| 2013/0131869 A1 | 5/2013 | Majewski et al. |
| 2013/0157493 A1 | 6/2013 | Brown |
| 2013/0158790 A1 | 6/2013 | McIntyre, Jr. et al. |
| 2013/0182308 A1 | 7/2013 | Guarr et al. |
| 2013/0194141 A1 | 8/2013 | Okajima et al. |
| 2013/0196600 A1 | 8/2013 | Capers et al. |
| 2013/0226353 A1 | 8/2013 | Park |
| 2013/0241299 A1 | 9/2013 | Snyker et al. |
| 2013/0242370 A1 | 9/2013 | Wang |
| 2013/0243120 A1 | 9/2013 | Tsai et al. |
| 2013/0243425 A1 | 9/2013 | Franklin |
| 2013/0250422 A1 | 9/2013 | Tandler |
| 2013/0263510 A1 | 10/2013 | Gassion |
| 2013/0271812 A1 | 10/2013 | Brown et al. |
| 2013/0271813 A1 | 10/2013 | Brown |
| 2013/0271814 A1 | 10/2013 | Brown |
| 2013/0271815 A1 | 10/2013 | Pradhan et al. |
| 2013/0277539 A1 | 10/2013 | Smilansky et al. |
| 2013/0278989 A1 | 10/2013 | Lam et al. |
| 2014/0007244 A1* | 1/2014 | Martin ............... G06F 21/577 726/25 |
| 2014/0008992 A1 | 1/2014 | Leabman |
| 2014/0043669 A1 | 2/2014 | Bergh et al. |
| 2014/0067733 A1 | 3/2014 | Humann |
| 2014/0101573 A1 | 4/2014 | Kuo |
| 2014/0149416 A1 | 5/2014 | Wallace |
| 2014/0156097 A1 | 6/2014 | Nesler et al. |
| 2014/0160550 A1 | 6/2014 | Brown et al. |
| 2014/0170863 A1 | 6/2014 | Brown |
| 2014/0172557 A1 | 6/2014 | Eden et al. |
| 2014/0177028 A1 | 6/2014 | Shrivastava et al. |
| 2014/0182350 A1 | 7/2014 | Bhavaraju et al. |
| 2014/0236323 A1 | 8/2014 | Brown et al. |
| 2014/0240474 A1 | 8/2014 | Kondo |
| 2014/0247475 A1 | 9/2014 | Parker et al. |
| 2014/0249876 A1 | 9/2014 | Wu et al. |
| 2014/0259931 A1 | 9/2014 | Plummer |
| 2014/0268287 A1 | 9/2014 | Brown et al. |
| 2014/0274458 A1 | 9/2014 | Kronenberg et al. |
| 2014/0300945 A1 | 10/2014 | Parker |
| 2014/0303788 A1 | 10/2014 | Sanders et al. |
| 2014/0317514 A1 | 10/2014 | Bokotey |
| 2014/0319116 A1 | 10/2014 | Fischer et al. |
| 2014/0330538 A1 | 11/2014 | Conklin et al. |
| 2014/0333485 A1 | 11/2014 | Stone et al. |
| 2014/0347190 A1 | 11/2014 | Grimm |
| 2014/0349497 A1 | 11/2014 | Brown et al. |
| 2014/0367057 A1 | 12/2014 | Feldstein |
| 2014/0368048 A1 | 12/2014 | Leabman et al. |
| 2014/0368899 A1 | 12/2014 | Greer |
| 2014/0371931 A1 | 12/2014 | Lin et al. |
| 2015/0002919 A1 | 1/2015 | Jack et al. |
| 2015/0003822 A1 | 1/2015 | Fukada et al. |
| 2015/0023661 A1 | 1/2015 | Borkenhagen et al. |
| 2015/0032264 A1 | 1/2015 | Emmons et al. |
| 2015/0049378 A1 | 2/2015 | Shrivastava et al. |
| 2015/0060648 A1 | 3/2015 | Brown et al. |
| 2015/0070745 A1 | 3/2015 | Pradhan |
| 2015/0098121 A1 | 4/2015 | Turnbull et al. |
| 2015/0106121 A1* | 4/2015 | Muhsin ............... G16H 50/30 705/3 |
| 2015/0109653 A1 | 4/2015 | Greer et al. |
| 2015/0110991 A1 | 4/2015 | Miwa et al. |
| 2015/0116808 A1 | 4/2015 | Branda et al. |
| 2015/0116811 A1 | 4/2015 | Shrivastava et al. |
| 2015/0120297 A1 | 4/2015 | Meruva |
| 2015/0122474 A1 | 5/2015 | Petersen |
| 2015/0129140 A1 | 5/2015 | Dean et al. |
| 2015/0155737 A1 | 6/2015 | Mayo |
| 2015/0160525 A1 | 6/2015 | Shi |
| 2015/0160965 A1 | 6/2015 | Archer et al. |
| 2015/0185581 A1 | 7/2015 | Pradhan et al. |
| 2015/0195644 A1 | 7/2015 | Wilson et al. |
| 2015/0198640 A1 | 7/2015 | Lee |
| 2015/0219975 A1 | 8/2015 | Phillips et al. |
| 2015/0222126 A1 | 8/2015 | Leabman et al. |
| 2015/0225999 A1 | 8/2015 | Berman et al. |
| 2015/0253367 A1 | 9/2015 | Flammer, III et al. |
| 2015/0255651 A1 | 9/2015 | Barr et al. |
| 2015/0270823 A1 | 9/2015 | Sobolewski |
| 2015/0293422 A1 | 10/2015 | Pradhan et al. |
| 2015/0323287 A1 | 11/2015 | Durand |
| 2015/0323915 A1 | 11/2015 | Warren et al. |
| 2015/0327010 A1 | 11/2015 | Gottschalk et al. |
| 2015/0355520 A1 | 12/2015 | Chung et al. |
| 2015/0362819 A1 | 12/2015 | Bjornard et al. |
| 2015/0378230 A1 | 12/2015 | Gudmunson et al. |
| 2015/0378231 A1 | 12/2015 | Greer et al. |
| 2015/0378715 A1 | 12/2015 | Solnit et al. |
| 2016/0020647 A1 | 1/2016 | Leabman et al. |
| 2016/0028162 A1 | 1/2016 | Ou et al. |
| 2016/0054633 A1 | 2/2016 | Brown et al. |
| 2016/0054634 A1 | 2/2016 | Brown et al. |
| 2016/0070151 A1 | 3/2016 | Shrivastava et al. |
| 2016/0071183 A1 | 3/2016 | Joshi et al. |
| 2016/0090098 A1 | 3/2016 | Kim et al. |
| 2016/0091769 A1 | 3/2016 | Rozbicki |
| 2016/0109778 A1 | 4/2016 | Shrivastava et al. |
| 2016/0124283 A1 | 5/2016 | Brown et al. |
| 2016/0134932 A1 | 5/2016 | Karp et al. |
| 2016/0147100 A1 | 5/2016 | Van Oosten et al. |
| 2016/0149635 A1 | 5/2016 | Hinman et al. |
| 2016/0154290 A1 | 6/2016 | Brown et al. |
| 2016/0181873 A1 | 6/2016 | Mitcheson et al. |
| 2016/0183056 A1 | 6/2016 | Leabman |
| 2016/0202589 A1 | 7/2016 | Nagel et al. |
| 2016/0203403 A1 | 7/2016 | Nagel et al. |
| 2016/0210711 A1 | 7/2016 | Krupa et al. |
| 2016/0225832 A1 | 8/2016 | Kwon et al. |
| 2016/0231755 A1 | 8/2016 | Ajax et al. |
| 2016/0248270 A1 | 8/2016 | Zeine et al. |
| 2016/0261837 A1 | 9/2016 | Thompson et al. |
| 2016/0359965 A1 | 12/2016 | Murphy et al. |
| 2016/0363799 A1 | 12/2016 | West et al. |
| 2016/0376831 A1 | 12/2016 | Plummer |
| 2017/0010880 A1 | 1/2017 | Yamazaki |
| 2017/0039339 A1 | 2/2017 | Bitran et al. |
| 2017/0052753 A1 | 2/2017 | Paolini, Jr. et al. |
| 2017/0063429 A1 | 3/2017 | Flask |
| 2017/0075183 A1 | 3/2017 | Brown |
| 2017/0075323 A1 | 3/2017 | Shrivastava et al. |
| 2017/0080341 A1 | 3/2017 | Mao et al. |
| 2017/0082903 A1 | 3/2017 | Vigano et al. |
| 2017/0085834 A1 | 3/2017 | Kim et al. |
| 2017/0097259 A1 | 4/2017 | Brown et al. |
| 2017/0104374 A1 | 4/2017 | Zeine et al. |
| 2017/0117754 A1 | 4/2017 | Noori et al. |
| 2017/0122802 A1 | 5/2017 | Brown et al. |
| 2017/0131610 A1 | 5/2017 | Brown et al. |
| 2017/0131611 A1 | 5/2017 | Brown et al. |
| 2017/0139301 A1 | 5/2017 | Messere et al. |
| 2017/0146884 A1 | 5/2017 | Vigano et al. |
| 2017/0161911 A1 | 6/2017 | Kumar et al. |
| 2017/0197494 A1 | 7/2017 | Li |
| 2017/0200424 A1 | 7/2017 | Xu et al. |
| 2017/0212400 A1 | 7/2017 | Shrivastava et al. |
| 2017/0234067 A1 | 8/2017 | Fasi et al. |
| 2017/0243122 A1 | 8/2017 | Komatsu et al. |
| 2017/0248564 A1 | 8/2017 | Miyajima |
| 2017/0251488 A1 | 8/2017 | Urban et al. |
| 2017/0253801 A1 | 9/2017 | Bae et al. |
| 2017/0264865 A1 | 9/2017 | Huangfu |
| 2017/0272145 A1 | 9/2017 | Lilja |

(56) References Cited

U.S. PATENT DOCUMENTS

| | | |
|---|---|---|
| 2017/0272317 A1 | 9/2017 | Singla et al. |
| 2017/0276542 A1 | 9/2017 | Klawuhn et al. |
| 2017/0279930 A1 | 9/2017 | Zhang |
| 2017/0285432 A1 | 10/2017 | Shrivastava et al. |
| 2017/0285433 A1 | 10/2017 | Shrivastava et al. |
| 2017/0347129 A1 | 11/2017 | Levi et al. |
| 2017/0364395 A1 | 12/2017 | Shrivastava et al. |
| 2017/0365908 A1 | 12/2017 | Hughes et al. |
| 2017/0374255 A1 | 12/2017 | Campbell et al. |
| 2017/0374437 A1 | 12/2017 | Schwarzkopf et al. |
| 2018/0088432 A1 | 3/2018 | Shrivastava et al. |
| 2018/0090992 A1 | 3/2018 | Shrivastava et al. |
| 2018/0095337 A1 | 4/2018 | Rozbicki et al. |
| 2018/0113986 A1 | 4/2018 | Zhu |
| 2018/0119973 A1 | 5/2018 | Rothman et al. |
| 2018/0129172 A1 | 5/2018 | Shrivastava et al. |
| 2018/0130455 A1 | 5/2018 | Plummer et al. |
| 2018/0138576 A1 | 5/2018 | Cohen |
| 2018/0139517 A1 | 5/2018 | Schwartz et al. |
| 2018/0144712 A1 | 5/2018 | Threlkel et al. |
| 2018/0153454 A1 | 6/2018 | Hayter et al. |
| 2018/0156484 A1 | 6/2018 | Kim et al. |
| 2018/0181085 A1 | 6/2018 | Gabriel et al. |
| 2018/0187484 A1 | 7/2018 | Hebeisen et al. |
| 2018/0189117 A1 | 7/2018 | Shrivastava et al. |
| 2018/0195752 A1 | 7/2018 | Sasaki et al. |
| 2018/0225585 A1 | 8/2018 | Dong et al. |
| 2018/0259373 A1 | 9/2018 | Staton et al. |
| 2018/0267380 A1 | 9/2018 | Shrivastava et al. |
| 2018/0269974 A1 | 9/2018 | Luciano |
| 2018/0284555 A1 | 10/2018 | Klawuhn et al. |
| 2018/0287780 A1 | 10/2018 | Safford et al. |
| 2018/0301783 A1 | 10/2018 | Bulja et al. |
| 2018/0306609 A1 | 10/2018 | Agarwal et al. |
| 2018/0307114 A1 | 10/2018 | Brown et al. |
| 2018/0321042 A1 | 11/2018 | Brewer et al. |
| 2018/0335939 A1 | 11/2018 | Karunamuni et al. |
| 2018/0349710 A1 | 12/2018 | Houri et al. |
| 2018/0364654 A1 | 12/2018 | Locke et al. |
| 2019/0011798 A9 | 1/2019 | Brown et al. |
| 2019/0025661 A9 | 1/2019 | Brown et al. |
| 2019/0025805 A1 | 1/2019 | Celia et al. |
| 2019/0036209 A1 | 1/2019 | Au |
| 2019/0044606 A1 | 2/2019 | Mansikkamaki |
| 2019/0049812 A1 | 2/2019 | Brown |
| 2019/0058977 A1 | 2/2019 | Gherardi et al. |
| 2019/0067826 A1 | 2/2019 | Achour et al. |
| 2019/0097827 A1 | 3/2019 | Angle et al. |
| 2019/0155122 A1 | 5/2019 | Brown et al. |
| 2019/0178511 A1 | 6/2019 | Zimmerman et al. |
| 2019/0203528 A1 | 7/2019 | Vigano et al. |
| 2019/0205774 A1 | 7/2019 | Ba et al. |
| 2019/0219881 A1 | 7/2019 | Shrivastava et al. |
| 2019/0229768 A1 | 7/2019 | Jeremy et al. |
| 2019/0235451 A1 | 8/2019 | Shrivastava et al. |
| 2019/0257143 A1 | 8/2019 | Nagel et al. |
| 2019/0267840 A1 | 8/2019 | Rozbicki et al. |
| 2019/0271895 A1 | 9/2019 | Shrivastava et al. |
| 2019/0294017 A1 | 9/2019 | Vigano et al. |
| 2019/0294018 A1 | 9/2019 | Shrivastava et al. |
| 2019/0317458 A1 | 10/2019 | Shrivastava et al. |
| 2019/0319335 A1 | 10/2019 | Hughes et al. |
| 2019/0324341 A1 | 10/2019 | Tonar et al. |
| 2019/0324431 A1 | 10/2019 | Cella et al. |
| 2019/0331978 A1 | 10/2019 | Shrivastava et al. |
| 2019/0346170 A1 | 11/2019 | Benefield |
| 2019/0347141 A1 | 11/2019 | Shrivastava et al. |
| 2019/0353972 A1 | 11/2019 | Shrivastava et al. |
| 2019/0354071 A1 | 11/2019 | Turney et al. |
| 2019/0356508 A1 | 11/2019 | Trikha et al. |
| 2019/0384652 A1 | 12/2019 | Shrivastava et al. |
| 2020/0004096 A1 | 1/2020 | Brown et al. |
| 2020/0019622 A1 | 1/2020 | Lu et al. |
| 2020/0026141 A1 | 1/2020 | Brown et al. |
| 2020/0041963 A1 | 2/2020 | Shrivastava et al. |
| 2020/0041967 A1 | 2/2020 | Shrivastava et al. |
| 2020/0045261 A1 | 2/2020 | Lim et al. |
| 2020/0057421 A1 | 2/2020 | Trikha et al. |
| 2020/0090089 A1 | 3/2020 | Aston et al. |
| 2020/0096775 A1 | 3/2020 | Franklin et al. |
| 2020/0103841 A1 | 4/2020 | Pillai et al. |
| 2020/0103894 A1 | 4/2020 | Celia et al. |
| 2020/0150508 A1 | 5/2020 | Patterson et al. |
| 2020/0176125 A1 | 6/2020 | Chatterjea et al. |
| 2020/0193155 A1 | 6/2020 | Keohane et al. |
| 2020/0209057 A1 | 7/2020 | Brown et al. |
| 2020/0227159 A1 | 7/2020 | Boisvert et al. |
| 2020/0241379 A1 | 7/2020 | Barnum et al. |
| 2020/0257179 A1 | 8/2020 | Barnum et al. |
| 2020/0259237 A1 | 8/2020 | Shrivastava et al. |
| 2020/0278245 A1 | 9/2020 | Brown et al. |
| 2020/0318426 A1 | 10/2020 | Vigano et al. |
| 2020/0321682 A1 | 10/2020 | Hughes et al. |
| 2020/0387041 A1 | 12/2020 | Shrivastava et al. |
| 2020/0390402 A1 | 12/2020 | Fernando |
| 2020/0410226 A1 | 12/2020 | Roth et al. |
| 2021/0010693 A1 | 1/2021 | Gamroth et al. |
| 2021/0021788 A1 | 1/2021 | McNelley et al. |
| 2021/0040789 A1 | 2/2021 | Rozbicki et al. |
| 2021/0055619 A1 | 2/2021 | Brown |
| 2021/0063834 A1 | 3/2021 | Brown et al. |
| 2021/0063835 A1 | 3/2021 | Vigano et al. |
| 2021/0072611 A1 | 3/2021 | Brown |
| 2021/0119318 A1 | 4/2021 | Hughes et al. |
| 2021/0165696 A1 | 6/2021 | Shrivastava et al. |
| 2021/0191221 A1 | 6/2021 | Shrivastava et al. |
| 2021/0210053 A1 | 7/2021 | Ng et al. |
| 2021/0232015 A1 | 7/2021 | Brown et al. |
| 2021/0246719 A1 | 8/2021 | Shrivastava et al. |
| 2021/0302799 A1 | 9/2021 | Khanna |
| 2021/0373511 A1 | 12/2021 | Shrivastava et al. |
| 2021/0376445 A1 | 12/2021 | Shrivastava et al. |
| 2021/0383804 A1 | 12/2021 | Makker et al. |
| 2021/0384764 A1 | 12/2021 | Shrivastava et al. |
| 2021/0390953 A1 | 12/2021 | Makker et al. |
| 2021/0405493 A1 | 12/2021 | Tinianov et al. |
| 2022/0011729 A1 | 1/2022 | Shrivastava et al. |
| 2022/0019117 A1 | 1/2022 | Shrivastava et al. |
| 2022/0021099 A1 | 1/2022 | Shrivastava et al. |
| 2022/0026267 A1 | 1/2022 | Brown et al. |
| 2022/0091469 A1 | 3/2022 | Brown et al. |
| 2022/0121078 A1 | 4/2022 | Vollen et al. |
| 2022/0159077 A1 | 5/2022 | Shrivastava et al. |
| 2022/0171248 A1 | 6/2022 | Shrivastava et al. |
| 2022/0179275 A1 | 6/2022 | Patterson et al. |
| 2022/0187667 A1 | 6/2022 | Nagel |
| 2022/0214652 A1 | 7/2022 | Trikha et al. |
| 2022/0231396 A1 | 7/2022 | Rozbicki et al. |
| 2022/0231399 A1 | 7/2022 | Brown et al. |
| 2022/0244608 A1 | 8/2022 | Brown et al. |
| 2022/0244610 A1 | 8/2022 | Tinianov et al. |
| 2022/0252952 A1 | 8/2022 | Rozbicki et al. |
| 2022/0255351 A1 | 8/2022 | Rozbicki et al. |
| 2022/0298850 A1 | 9/2022 | Shrivastava et al. |
| 2022/0316269 A1 | 10/2022 | Shrivastava et al. |

FOREIGN PATENT DOCUMENTS

| | | |
|---|---|---|
| CN | 1219251 A | 6/1999 |
| CN | 1267416 A | 9/2000 |
| CN | 1311935 A | 9/2001 |
| CN | 2590732 Y | 12/2003 |
| CN | 1692348 A | 11/2005 |
| CN | 1723658 A | 1/2006 |
| CN | 101032052 A | 9/2007 |
| CN | 101128783 A | 2/2008 |
| CN | 101154104 A | 4/2008 |
| CN | 101253460 A | 8/2008 |
| CN | 101401312 A | 4/2009 |
| CN | 101501757 A | 8/2009 |
| CN | 101510078 A | 8/2009 |
| CN | 101707892 A | 5/2010 |
| CN | 101856193 A | 10/2010 |
| CN | 101868346 A | 10/2010 |

(56) References Cited

FOREIGN PATENT DOCUMENTS

| | | |
|---|---|---|
| CN | 101969207 A | 2/2011 |
| CN | 102063116 A | 5/2011 |
| CN | 102203370 A | 9/2011 |
| CN | 102255119 A | 11/2011 |
| CN | 102414601 A | 4/2012 |
| CN | 102598469 A | 7/2012 |
| CN | 202443309 U | 9/2012 |
| CN | 103051737 A | 4/2013 |
| CN | 103119845 A | 5/2013 |
| CN | 103155330 A | 6/2013 |
| CN | 203019761 U | 6/2013 |
| CN | 103238107 A | 8/2013 |
| CN | 103282841 A | 9/2013 |
| CN | 103283102 A | 9/2013 |
| CN | 103327126 A | 9/2013 |
| CN | 203204328 U | 9/2013 |
| CN | 103345236 A | 10/2013 |
| CN | 103547965 A | 1/2014 |
| CN | 103557579 A | 2/2014 |
| CN | 103649826 A | 3/2014 |
| CN | 103842735 A | 6/2014 |
| CN | 103987909 A | 8/2014 |
| CN | 104102060 A | 10/2014 |
| CN | 104321497 A | 1/2015 |
| CN | 104335595 A | 2/2015 |
| CN | 104364706 A | 2/2015 |
| CN | 204302976 U | 4/2015 |
| CN | 104603686 A | 5/2015 |
| CN | 104778365 A | 7/2015 |
| CN | 104781493 A | 7/2015 |
| CN | 104884248 A | 9/2015 |
| CN | 105143586 A | 12/2015 |
| CN | 105424840 A | 3/2016 |
| CN | 105431772 A | 3/2016 |
| CN | 106125444 A | 11/2016 |
| CN | 106164973 A | 11/2016 |
| CN | 205743507 U | 11/2016 |
| CN | 106225163 A | 12/2016 |
| CN | 106462023 A | 2/2017 |
| CN | 106575064 A | 4/2017 |
| CN | 107655518 A | 2/2018 |
| CN | 107850815 A | 3/2018 |
| CN | 104730795 B | 5/2018 |
| CN | 108231195 A | 6/2018 |
| CN | 108414682 A | 8/2018 |
| CN | 108769186 A | 11/2018 |
| CN | 110389095 A | 10/2019 |
| CN | 110864435 A | 3/2020 |
| CN | 111089404 A | 5/2020 |
| CN | 111102694 A | 5/2020 |
| CN | 112113603 A | 12/2020 |
| DE | 10124673 A1 | 11/2002 |
| EP | 0413580 A1 | 2/1991 |
| EP | 0445314 A1 | 9/1991 |
| EP | 0588514 A1 | 3/1994 |
| EP | 0869032 A2 | 10/1998 |
| EP | 0917667 A1 | 5/1999 |
| EP | 0920210 A1 | 6/1999 |
| EP | 1012633 B1 | 3/2002 |
| EP | 0835475 B1 | 9/2004 |
| EP | 1510854 A1 | 3/2005 |
| EP | 1417535 B1 | 11/2005 |
| EP | 1619546 A2 | 1/2006 |
| EP | 1626306 A2 | 2/2006 |
| EP | 1929701 A2 | 6/2008 |
| EP | 1297380 B1 | 11/2008 |
| EP | 2090961 A1 | 8/2009 |
| EP | 2161615 A1 | 3/2010 |
| EP | 2267966 A2 | 12/2010 |
| EP | 2357544 A2 | 8/2011 |
| EP | 2648086 A2 | 10/2013 |
| EP | 2733998 A1 | 5/2014 |
| EP | 2764998 A1 | 8/2014 |
| EP | 2357544 B1 | 10/2014 |
| EP | 2851993 A1 | 3/2015 |
| EP | 2955815 A1 | 12/2015 |
| EP | 3015915 A1 | 5/2016 |
| EP | 2837205 B1 | 2/2017 |
| EP | 3242587 A1 | 11/2017 |
| EP | 3293941 A1 | 3/2018 |
| EP | 3299957 A1 | 3/2018 |
| EP | 3328000 A1 | 5/2018 |
| EP | 3352053 A1 | 7/2018 |
| EP | 3788769 A1 | 3/2021 |
| FR | 2643512 A1 | 8/1990 |
| FR | 2855291 A1 | 11/2004 |
| JP | S63208830 A | 8/1988 |
| JP | S63271320 A | 11/1988 |
| JP | H02132420 A | 5/1990 |
| JP | H05178645 A | 7/1993 |
| JP | H0611477 A | 1/1994 |
| JP | H06308073 A | 11/1994 |
| JP | H1063216 A | 3/1998 |
| JP | H10215492 A | 8/1998 |
| JP | H10233612 A | 9/1998 |
| JP | H11500838 A | 1/1999 |
| JP | 2001196826 A | 7/2001 |
| JP | 2003284160 A | 10/2003 |
| JP | 2004245985 A | 9/2004 |
| JP | 2005303348 A | 10/2005 |
| JP | 2006252886 A | 9/2006 |
| JP | 2006287729 A | 10/2006 |
| JP | 2007156909 A | 6/2007 |
| JP | 4139109 B2 | 8/2008 |
| JP | 2008542578 A | 11/2008 |
| JP | 4351914 B2 | 10/2009 |
| JP | 2011008271 A | 1/2011 |
| JP | 4694816 B2 | 6/2011 |
| JP | 4799113 B2 | 10/2011 |
| JP | 2012533060 A | 12/2012 |
| JP | 2013057975 A | 3/2013 |
| JP | 2013515457 A | 5/2013 |
| JP | 2014204550 A | 10/2014 |
| JP | 2015128349 A | 7/2015 |
| JP | 2016512677 A | 4/2016 |
| JP | 2018507337 A | 3/2018 |
| JP | 2019186771 A | 10/2019 |
| JP | 6664190 B2 | 3/2020 |
| KR | 19990088613 | 12/1999 |
| KR | 20030040361 A | 5/2003 |
| KR | 20030073121 A | 9/2003 |
| KR | 200412640 Y1 | 3/2006 |
| KR | 100752041 B1 | 8/2007 |
| KR | 20080022319 A | 3/2008 |
| KR | 20090026181 A | 3/2009 |
| KR | 100904847 B1 | 6/2009 |
| KR | 20090066107 A | 6/2009 |
| KR | 100931183 B1 | 12/2009 |
| KR | 10-2021-00016666 A | 2/2010 |
| KR | 20100017542 A | 2/2010 |
| KR | 20100034361 A | 4/2010 |
| KR | 20110003698 A | 1/2011 |
| KR | 20110094672 A | 8/2011 |
| KR | 20110128213 A | 11/2011 |
| KR | 20120045915 A | 5/2012 |
| KR | 20120092921 A | 8/2012 |
| KR | 20120117409 A | 10/2012 |
| KR | 20130023668 A | 3/2013 |
| KR | 101323668 B1 | 11/2013 |
| KR | 101346862 B1 | 1/2014 |
| KR | 20140004175 A | 1/2014 |
| KR | 101608386 B1 | 4/2016 |
| KR | 101629809 B1 | 6/2016 |
| KR | 20170121858 A | 11/2017 |
| KR | 101799323 B1 | 12/2017 |
| KR | 20170134321 A | 12/2017 |
| KR | 20180012615 A | 2/2018 |
| KR | 101871991 B1 | 8/2018 |
| KR | 101990931 B1 | 6/2019 |
| KR | 102018182 B1 | 10/2019 |
| KR | 20210032133 A | 3/2021 |
| KR | 20210039721 A | 4/2021 |
| RU | 104808 U1 | 5/2011 |
| RU | 2012107324 A | 9/2013 |

(56) References Cited

FOREIGN PATENT DOCUMENTS

| | | |
|---|---|---|
| TW | 200532346 A | 10/2005 |
| TW | I243239 B | 11/2005 |
| TW | M368189 U | 11/2009 |
| TW | 201029838 A | 8/2010 |
| TW | 201215981 A | 4/2012 |
| TW | 201217999 A | 5/2012 |
| TW | I387734 B | 3/2013 |
| TW | 201344874 A | 11/2013 |
| TW | 201351010 A | 12/2013 |
| TW | 201403034 A | 1/2014 |
| TW | I430251 B | 3/2014 |
| TW | 201423773 A | 6/2014 |
| TW | 201447089 A | 12/2014 |
| TW | 201510605 A | 3/2015 |
| TW | M504418 U | 7/2015 |
| TW | 201606409 A | 2/2016 |
| TW | M519749 U | 4/2016 |
| TW | 201635840 A | 10/2016 |
| TW | I567469 B | 1/2017 |
| TW | I607269 B | 12/2017 |
| WO | WO-9816870 A1 | 4/1998 |
| WO | WO-9913359 A1 | 3/1999 |
| WO | WO-0065770 A1 | 11/2000 |
| WO | WO-0124700 A1 | 4/2001 |
| WO | WO-0182410 A1 | 11/2001 |
| WO | WO-0213052 A2 | 2/2002 |
| WO | WO-0241740 A1 | 5/2002 |
| WO | WO-02054086 A1 | 7/2002 |
| WO | WO-03037056 A1 | 5/2003 |
| WO | WO-03092309 A1 | 11/2003 |
| WO | WO-2004003649 A1 | 1/2004 |
| WO | WO-2005098811 A1 | 10/2005 |
| WO | WO-2005103807 A2 | 11/2005 |
| WO | WO-2006089718 A2 | 8/2006 |
| WO | WO-2007016546 A2 | 2/2007 |
| WO | WO-2007146862 A2 | 12/2007 |
| WO | WO-2008030018 A1 | 3/2008 |
| WO | WO-2008073372 A2 | 6/2008 |
| WO | WO-2008122906 A1 | 10/2008 |
| WO | WO-2008147322 A1 | 12/2008 |
| WO | WO-2009124647 A1 | 10/2009 |
| WO | WO-2010014648 A1 | 2/2010 |
| WO | WO-2010079388 A1 | 7/2010 |
| WO | WO-2010106648 A1 | 9/2010 |
| WO | WO-2010120771 A1 | 10/2010 |
| WO | WO-2011020478 A1 | 2/2011 |
| WO | WO-2011082208 A2 | 7/2011 |
| WO | WO-2011087684 A1 | 7/2011 |
| WO | WO-2011087687 A1 | 7/2011 |
| WO | WO-2011124720 A2 | 10/2011 |
| WO | WO-2011127015 A1 | 10/2011 |
| WO | WO-2012079159 A1 | 6/2012 |
| WO | WO-2012080618 A1 | 6/2012 |
| WO | WO-2012080656 A1 | 6/2012 |
| WO | WO-2012080657 A1 | 6/2012 |
| WO | WO-2012125332 A2 | 9/2012 |
| WO | WO-2012125348 A2 | 9/2012 |
| WO | WO-2012145155 A1 | 10/2012 |
| WO | WO-2013046112 A1 | 4/2013 |
| WO | WO-2013055457 A1 | 4/2013 |
| WO | WO-2013059674 A1 | 4/2013 |
| WO | WO-2013109881 A2 | 7/2013 |
| WO | WO-2013121103 A1 | 8/2013 |
| WO | WO-2013155467 A1 | 10/2013 |
| WO | WO-2013155612 A1 | 10/2013 |
| WO | WO-2013158365 A1 | 10/2013 |
| WO | WO-2013158464 A1 | 10/2013 |
| WO | WO-2013177575 A1 | 11/2013 |
| WO | WO-2014032023 A1 | 2/2014 |
| WO | WO-2014059268 A2 | 4/2014 |
| WO | WO-2014082092 A1 | 5/2014 |
| WO | WO-2014102198 A1 | 7/2014 |
| WO | WO-2014121809 A1 | 8/2014 |
| WO | WO-2014121863 A1 | 8/2014 |
| WO | WO-2014130471 A1 | 8/2014 |
| WO | WO-2014134451 A2 | 9/2014 |
| WO | WO-2014209812 A1 | 12/2014 |
| WO | WO-2015013578 A1 | 1/2015 |
| WO | WO-2015051262 A1 | 4/2015 |
| WO | WO-2015075007 A1 | 5/2015 |
| WO | WO-2015077097 A1 | 5/2015 |
| WO | WO-2015077829 A1 | 6/2015 |
| WO | WO-2015100419 A1 | 7/2015 |
| WO | WO-2015109378 A1 | 7/2015 |
| WO | WO-2015113592 A1 | 8/2015 |
| WO | WO-2015134789 A1 | 9/2015 |
| WO | WO-2015171886 A1 | 11/2015 |
| WO | WO-2016004109 A1 | 1/2016 |
| WO | WO-2016054112 A1 | 4/2016 |
| WO | WO-2016072620 A1 | 5/2016 |
| WO | WO-2016085964 A1 | 6/2016 |
| WO | WO-2016086017 A1 | 6/2016 |
| WO | WO-2016094445 A1 | 6/2016 |
| WO | WO-2016174228 A1 | 11/2016 |
| WO | WO-2016183059 A1 | 11/2016 |
| WO | WO-2017007841 A1 | 1/2017 |
| WO | WO-2017007942 A1 | 1/2017 |
| WO | WO-2017058568 A1 | 4/2017 |
| WO | WO-2017059362 A1 | 4/2017 |
| WO | WO-2017062915 A1 | 4/2017 |
| WO | WO-2017075059 A1 | 5/2017 |
| WO | WO-2017075472 A1 | 5/2017 |
| WO | WO-2017120262 A1 | 7/2017 |
| WO | WO-2017129855 A1 | 8/2017 |
| WO | WO-2017189618 A1 | 11/2017 |
| WO | WO-2017192881 A1 | 11/2017 |
| WO | WO-2018019473 A1 | 2/2018 |
| WO | WO-2018039080 A1 | 3/2018 |
| WO | WO-2018063919 A1 | 4/2018 |
| WO | WO-2018067377 A1 | 4/2018 |
| WO | WO-2018094203 A1 | 5/2018 |
| WO | WO-2018098089 A1 | 5/2018 |
| WO | WO-2018102103 A1 | 6/2018 |
| WO | WO-2018112095 A2 | 6/2018 |
| WO | WO-2018152249 A1 | 8/2018 |
| WO | WO-2018200702 A1 | 11/2018 |
| WO | WO-2018200740 A2 | 11/2018 |
| WO | WO-2018200752 A1 | 11/2018 |
| WO | WO-2019022129 A1 | 1/2019 |
| WO | WO-2019157602 A1 | 8/2019 |
| WO | WO-2019178282 A1 | 9/2019 |
| WO | WO-2019203931 A1 | 10/2019 |
| WO | WO-2019213441 A1 | 11/2019 |
| WO | WO-2020109963 A1 | 6/2020 |
| WO | WO-2020148479 A1 | 7/2020 |
| WO | WO-2020172187 A1 | 8/2020 |
| WO | WO-2020185941 A1 | 9/2020 |
| WO | WO-2020227702 A2 | 11/2020 |
| WO | WO-2020243690 A1 | 12/2020 |
| WO | WO-2020227702 A3 | 1/2021 |
| WO | WO-2021211798 A1 | 10/2021 |

OTHER PUBLICATIONS

"IAQ and Office Spaces: Adapting to New Regulations," Envio Systems, 6 pp., URL:https://enviosystems.com/2021/04/iaq-and-office-spaces-adapting-to-new-regulations/.
"Updated: This AI camera detects people who may have COVID-19," Fast Company, 9 pp., URL:https://www.fastcompany.com/90479220/this-ai-camera-detects-people-who-may-have-covid-19.
Saud Al-Humairi et al., "Opportunities and challenges for the building monitoring systems in the age-pandemic of COVID-19: Review and prospects," Innovative Infrastructure Solutions 6:79, 10 pp. (2021).
Rathore et al., "Urban planning and building smart cities based on the Internet of Things using Big Data analytics," Computer Networks 101:63-80 (2016).
"Smart Building Solutions," Pressac Communications, 4 pp., URL:https://www.pressac.com/.
"Optimize Space Utilitzation and Use," LineMetrics, 14 pp., URL: https://www.linemetrics.com/de/anwendungsfaelle/raumauslastung-und-nutzung/.

(56) References Cited

OTHER PUBLICATIONS

"Help Tenants with a Safe Office Comeback," Sharry, 11 pp. URL:https://www.sharry.tech/anti-covid/.
Aamidor, J., "Blockchain: coming to a smart building near you?", GreenTechMedia.com, Sep. 19, 2017, 5 pp. https://www.greentechmedia.com/articles/read/blockchain-coming-to-a-smart-building-near-you#gs.0jk23x retrieved Jan. 25, 2021.
AGC, Inc., "AGC completes development of 5G-compatible 'Glass Antenna that adds cellular base station capabilities to windows,'" Press Release, Jun. 3, 2020, 2 pp.
"Sage Product Highlights" screenshot, accessed Aug. 28, 2015, 1 page.
"SageGlass helps Solar Decathlon- and AIA award-winning home achieve net-zero energy efficiency" in MarketWatch.com, http://www.marketwatch.com/story/sageglass-helps-solar-decathlon-and-aia-award-winning-home-achieve-net-zero-energy-efficiency-2012-06-07, Jun. 7, 2012.
"SageGlass Mobile App" screenshot, accessed Aug. 28, 2015, 1 page.
"SageGlass Unplugged" screenshot, accessed Aug. 28, 2015, 1 page.
"SageGlass Unplugged™—wireless dynamic glass", 2014, 2 pages.
Alarifi, A. et al., "Ultra Wideband Indoor Positioning Technologies: Analysis and Recent Advances", Sensors, May 16, 2016, vol. 16 No. 5, pp. 1-36.
APC by Schneider Electric, Smart-UPS 120V Product Brochure, 2013, 8 pp.
AU Examination report dated Feb. 22, 2022, in Application No. AU2016346328.
AU Examination report dated Oct. 7, 2021, in AU Application No. 2016346328.
AU examination report dated Oct. 1, 2021, in application No. AU2020220165.
AU Office Action dated Jan. 11, 2022, in Application No. AU2021201145.
AU Office Action dated Jan. 24, 2022, in Application No. AU2020273368.
AU Office action dated Apr. 4, 2022, in AU Application No. AU2020226999.
AU Office Action dated Aug. 30, 2022, in Application No. AU20210250838.
AU Office Action dated Jul. 14, 2022, in Application No. AU2020273368.
AU Office action dated Oct. 22, 2021, in AU Application No. AU2020226999.
Australian Examination Report dated Apr. 4, 2016 in AU Application No. 2013249706.
Australian Examination Report dated Dec. 24, 2019 in AU Application No. 2015227056.
Australian Examination Report dated Jul. 10, 2019 in AU Application No. 2018203436.
Australian Examination Report dated Mar. 2, 2020 in AU Application No. 2015353569.
Australian Examination Report dated Nov. 21, 2019 in AU Application No. 2018260906.
Australian Examination Report No. 1 dated Nov. 9, 2017 in AU Application No. 2017200334.
Australian Examination Report No. 2 dated Apr. 5, 2018 in AU Application No. 2017200334.
Australian Examination Report No. 3 dated Nov. 6, 2018 in AU Application No. 2017200334.
Australian Office Action dated May 21, 2021 in AU Application No. 2016346328.
Australian Office Action dated Apr. 8, 2020 in AU Application No. 2015353606.
Australian Office Action dated Aug. 10, 2020 in AU Application No. 2015360714.
Australian Office Action dated Aug. 20, 2019 in AU Application No. 2015353606.
Australian Office Action dated Aug. 9, 2021 in AU Application No. 2015360714.
Australian Office Action dated Dec. 4, 2020 in AU Application No. 2015360714.
Australian Office Action dated Feb. 19, 2021 in AU Application No. 2017260101.
Australian Office Action dated Jun. 3, 2021 in AU Application No. AU 2020220165.
Australian Office Action dated Jun. 4, 2021 in AU Application No. 2015360714.
Australian Office Action dated Mar. 4, 2020 in AU Application No. 2015353606.
Australian Office Action dated May 10, 2019 in AU Application No. 2015353606.
Azini, A.S. et al., "Transparent Antenna Design for Wireless Access Point Application," PIERS Proceedings, Taipei, Mar. 25-28, 2013, pp. 910-913.
Balzano Q., et al., "RF Energy In Cars From Window-mounted Antennas", 36th IEEE Vehicular Technology Conference, 2006, pp. 32-39.
"Blockchain and the internet of things: the IoT blockchain opportunity and challenge," I-Scoop, Sep. 2016, rev. Feb. 2018, 16 pp. https://www.i-scoop.eu/blockchain-distributed-ledger-technology/blockchain-iot/ retrieved Feb. 20, 2019.
Bradley. A, "DeviceNet Media—Design and Installation Guide", Internet Citation, Jul. 1, 2004, pp. 128, XP002384552,Retrieved from the Internet:URL:http://literature.rockwellautomation.com/idc/groups/literature/documents/um/dnet-um072 -en-p.pdf[retrieved on Jun. 9, 2006].
Byun, J et al., "Development of a Self-adapting Intelligent System for Building Energy Saving and Context-aware Smart Services", IEEE Transactions on Consumer Electronics, Feb. 2011, vol. 57, No. 1, pp. 90-98.
CA Office Action dated Dec. 22, 2021, in Application No. 2968665.
CA Office Action dated Dec. 13, 2021, in Application No. CA2970300.
CA Office Action dated Dec. 23, 2021, in Application No. CA2941526.
CA Office action dated Nov. 10, 2021, in CA Application No. CA2870673.
CA Office Action dated Sep. 13, 2022, in Application No. CA2970300.
Canadian Examination Report dated Feb. 13, 2020 in CA Application No. 2,870,673.
Canadian Examination Report dated Jan. 18, 2019 in CA Application No. 2,870,673.
Cecilio, J., et al., "A configurable middleware for processing heterogenous industrial intelligent sensors," IEEE 16th International Conference on Intelligent Engineering Systems (INES), Jun. 15, 2012, pp. 145-149.
Chan, E.C.L, et al., "Effect of Channel Interference on Indoor Wireless Local Area Network Positioning" IEEE 6th International Conference on Wireless and Mobile Computing, Networking and Communications, Oct. 11, 2010, pp. 239-245.
Chen, H. et al. "The Design and Implementation of a Smart Building Control System", 2009 IEEE International Conference on e-Business Engineering, pp. 255-262.
Chinese Notice of Grant & Search Report dated May 8, 2017 in CN Application No. 201380030251.8.
Chinese Office Action & Search Report dated Aug. 3, 2020 in CN Application No. 201680060052.5.
Chinese Office Action & Search Report dated Mar. 25, 2021 in CN Application No. 201680060052.5.
Chinese Office Action dated Sep. 7, 2016 in CN Application No. 201380030251.8.
Chinese Office Action dated Dec. 23, 2020 in CN Application No. 201710564603.8.
Chinese Office Action dated Feb. 3, 2020 in CN Application No. 201710564603.8.
Chinese Office Action dated Jul. 2, 2021 in CN Application No. 201810573469.2.
Chinese Office Action dated Jul. 21, 2020 in CN Application No. 201710564603.8.
Chinese Office Action dated Mar. 26, 2015 in CN Application No. 201280060910.8.

(56) References Cited

OTHER PUBLICATIONS

Chinese Office Action dated Mar. 3, 2021 in CN Application No. 201810573469.2.
Chinese Office Action dated Mar. 5, 2019 in CN Application No. 201680068239.X.
Chinese Office Action dated May 7, 2020 in CN Application No. 201810573469.2.
Chinese Office Action dated Sep. 6, 2019 in CN Application No. 201680068239.X.
CN Office Action dated Aug. 1, 2022, in Application No. CN201880037591.6 With English translation.
CN Office action dated Aug. 22, 2022 in Application No. CN202011547257.0 With English translation.
CN Office Action dated Aug. 31, 2022 in Application No. CN201780069604.3.
CN Office Action dated Dec. 29, 2021, in application No. 202010466929.9 with English translation.
CN Office Action dated May 5, 2022, in Application No. CN201780080267.8 With English Translation.
CN Notice of Allowance with Supplemental Search Report (w/translation) dated Mar. 1, 2021 in CN Application No. 201580040461.4.
CN Office Action dated May 6, 2022 in Application No. CN202010475742 With English Translation.
CN Office Action dated May 17, 2022, in Application No. CN201780069604.3 With English Translation.
CN Office Action dated Apr. 15, 2022 in CN Application No. 201780063202.2.
CN Office Action dated Apr. 18, 2022, in Application No. CN202011547257.0 with English translation.
CN Office Action dated Apr. 27, 2022, in Application No. CN201780057293.9 with English translation.
CN Office Action dated Apr. 29, 2020 in CN Application No. 201780038353.2.
CN Office Action dated Apr. 6, 2021 in CN Application No. 201780038353.2.
CN Office Action dated Apr. 6, 2021 in CN Application No. 201911227990.1.
CN Office Action dated Aug. 16, 2019 in CN Application No. 201580015979.2.
CN Office Action dated Aug. 19, 2022, in Application No. CN202080022001.X with English translation.
CN Office Action dated Aug. 2, 2021, in CN Application No. 201780038353.2.
CN Office Action dated Aug. 28, 2018 in CN Application No. 201580070776.3.
CN Office Action dated Aug. 3, 2021 in CN Application No. 201780063202.2.
CN Office Action dated Aug. 6, 2019 in CN Application No. 201580070207.9.
CN Office Action dated Dec. 1, 2021, in application No. CN201780069604.3 with English translation.
CN Office Action dated Feb. 16, 2022, in CN Application No. 201680060052.5 with English Translation.
CN Office Action dated Feb. 2, 2019 in CN Application No. 201580015979.2.
CN Office Action dated Feb. 3, 2020 in CN Application No. 201580072749.X.
CN Office Action dated Jan. 15, 2020 in CN Application No. 201580015979.2.
CN Office Action dated Jul. 28, 2021, in CN Application No. 201680060052.5.
CN Office Action dated Jul. 28, 2021, in CN Application No. 201780057293.9.
CN Office Action dated Jun. 29, 2021 in CN Application No. 202010466929.9.
CN Office Action dated Jun. 3, 2020 in CN Application No. 201580015979.2.
CN Office Action dated Jun. 3, 2021 in CN Application No. 201580072749.X.
CN Office Action dated Mar. 19, 2019 in CN Application No. 201580070776.3.
CN Office Action dated Mar. 2, 2022, in Application No. CN201880037591.6 with English translation.
CN Office Action dated Mar. 5, 2019 in CN Application No. 201580070207.9.
CN Office Action dated Mar. 8, 2021 in CN Application No. 201580072749.X.
CN Office Action dated Mar. 9, 2020 in CN Application No. 201580040461.4.
CN Office Action dated May 20, 2022, in Application No. CN202010466929.9 with English translation.
CN Office Action dated Nov. 12, 2021, in Application No. CN20158072749 with English translation.
CN Office Action dated Nov. 6, 2020 in CN Application No. 201780038353.2.
CN Office Action dated Oct. 21, 2020 in CN Application No. 201580040461.4.
CN Office Action dated Oct. 22, 2020 in CN Application No. 201911227990.1.
CN Office Action dated Oct. 9, 2019 in CN Application No. 201580070776.3.
CN Office Action dated Sep. 15, 2021, in application No. CN201911227990.1.
CN Office Action dated Sep. 28, 2021, in application No. CN201780080267.8 with English translation.
CN Office Action dated Sep. 3, 2021, in CN Application No. CN202010475742.5 with English translation.
CN Office Action dated Sep. 30, 2020 in CN Application No. 201580072749.X.
Communication re Third-Party Observation dated Dec. 4, 2014 and Third-Party Observation dated Dec. 3, 2014 in PCT/US2014/016974.
Dang, T. et al., "An Approach to Data Privacy in Smart Home using Blockchain Technology", International Conference on Advanced Computing and Applications, IEEE, Nov. 27, 2018, pp. 58-64.
Duchon, Claude E. et al., "Estimating Cloud Type from Pyranometer Observations," Journal of Applied Meteorology, vol. 38, Jan. 1999, pp. 132-141.
EP Office Action dated Jul. 13, 2022 in Application No. EP20170858928.
EP Office Action dated Sep. 12, 2022 in Application No. EP20180791117.7.
EP Examination Report dated Mar. 4, 2019 in EP Application No. 15814233.1.
EP Extended European Search Report dated Sep. 14, 2021, in the application EP21182449.7.
EP Extended Search Report dated Dec. 17, 2019 in EP Application No. 19202054.
EP Extended Search Report dated Dec. 4, 2019 in EP Application No. 17793364.5.
EP Extended Search Report dated Feb. 15, 2018 in EP Application No. 15814233.1.
EP Extended Search Report dated Feb. 25, 2020 in EP Application No. 17844188.7.
EP Extended Search Report dated Jun. 19, 2017 in EP Application No. 15758538.1.
EP Extended Search Report dated Jun. 5, 2018 in EP Application No. 15868003.3.
EP Extended Search Report dated Mar. 31, 2020 in EP Application No. 17857230.1.
EP Extended Search Report dated Nov. 11, 2020 in EP Application No. 18791117.7.
EP Extended Search Report dated Nov. 28, 2019 in EP Application No. 19188907.0.
EP Extended Search Report dated Nov. 8, 2018 in EP Application No. 15863112.7.
EP Extended Search Report dated Oct. 1, 2020 in EP Application No. 17858928.9.
EP Extended Search Report dated Sep. 6, 2018 in EP Application No. 15863433.7.
EP Office Action dated Jan. 17, 2022, in Application No. 17858928.9.

(56) References Cited

OTHER PUBLICATIONS

EP Office Action dated Jun. 30, 2022 in Application No. EP20190727174.
EP Office Action dated Aug. 21, 2018 in EP Application No. 15758538.1.
EP office action dated Aug. 25, 2021, in EP Application No. EP19202054.3.
EP Office Action dated Dec. 16, 2021, in Application No. EP17793364.5.
EP Office Action dated Feb. 15, 2022, in Application No. EP19188907.0.
EP Office Action dated Jan. 29, 2021 in EP Application No. 15868003.3.
EP Office Action dated Jun. 3, 2022, in Application No. EP19713970.2.
EP Office Action dated May 14, 2020 in EP Application No. 15868003.3.
EP Office Action dated Nov. 19, 2020 in EP Application No. 15758538.1.
EP Office Action dated Oct. 1, 2021, in application No. EP17857230.1.
EP Office Action dated Sep. 30, 2021, in application No. EP19185576.6.
EP Partial Supplementary Search Report dated May 23, 2018 in EP Application No. 15863433.7.
EP Search Report dated Dec. 10, 2021, in Application No. EP19787808.5.
European Decision to Refuse dated Jun. 6, 2019 in EP Application No. 13777692.8.
European Extended Search Report dated Apr. 18, 2019 in EP Application No. 16847427.8.
European Extended Search Report dated Dec. 13, 2019 in EP Application No. 19185576.6.
European Extended Search Report dated Jan. 25, 2016 in EP Application No. 13777692.8.
European Extended Search Report dated Jul. 3, 2020 in EP Application No. 17875406.5.
European Extended Search Report dated May 31, 2019 in EP Application No. 16860691.1.
European Office Action dated Apr. 8, 2020 in EP Application No. 18186062.8.
European Office Action dated Feb. 25, 2021 in EP Application No. 15863112.7.
European Office Action dated Jul. 8, 2020 in EP Application No. 15863433.7.
European Office Action dated Mar. 11, 2021 in EP Application No. 16860691.1.
European Office Action dated Mar. 31, 2017 in EP Application No. 13777692.8.
European Office Action dated Mar. 4, 2021 in EP Application No. 16847427.8.
European Office Action dated May 7, 2021 in EP Application No. 15863433.7.
European Office Action dated Oct. 17, 2019 in EP Application No. 15863433.7.
European Office Action dated Sep. 26, 2022 in Application No. EP18186062.8.
European Partial Search Report dated Oct. 6, 2015 in EP Application No. 13777692.8.
European Search Report dated Aug. 11, 2014 in European Application No. 12757877.1.
European Search Report dated Jul. 23, 2014 in European Application No. 12756917.6.
European Search Report dated Jul. 29, 2014 in European Application No. 12758250.0.
European Search Report dated Mar. 5, 2015 in European Application No. 12841714.4.
European Summons to Oral Proceedings dated Jun. 27, 2018 in EP Application No. 13777692.8.
Examiner's Answer dated Jan. 27, 2017 in U.S. Appl. No. 13/449,248.
Examiner's Answer dated Nov. 28, 2016 in U.S. Appl. No. 13/449,251.
Extended European Search Report dated Nov. 30, 2018 in EP Application No. 18186062.8.
Extended European Search Report dated Nov. 29, 2021, in the application EP21185911.1.
Final Office Action dated Jun. 5, 2015 in U.S. Appl. No. 13/968,258.
Graham, Steve, "Clouds & Radiation," Mar. 1, 1999. [http://earthobservatory.nasa.gov/Features/Clouds/].
Haby, Jeff, "Cloud Detection (IR v. VIS)," (known as of Sep. 3, 2014) [http://theweatherprediction.com/habyhints2/512/].
Hameed, Z. et al., "Condition Monitoring and Fault Detection of Wind Turbines and Related Algorithms: a Review.", Renewable and Sustainable energy reviews, 2009, vol. 13, pp. 1-39.
Hoosier Energy, "How do they do that? Measuring Real-Time Cloud Activity" Hoosier Energy Current Connections, (known as of Sep. 3, 2014). (http://members.questline.com/Article.aspx?articleID=18550&accountID=196000&nl=11774).
"How Cleantech wants to make a 2012 comeback" http://mountainview.patch.com/articles/how-cleantech-wants-to-make-a-2012-comeback, Jan. 23, 2012.
IN Office Action dated Aug. 5, 2022 In Application No. IN201937050525.
IN Office Action dated May 10, 2022, in Application No. IN202037043494.
IN Office Action dated Jan. 13, 2022, in Application No. 201937044701.
IN Office Action dated Aug. 2, 2021 in IN Application No. 201637028587.
IN Office Action dated Dec. 24, 2021, in Application No. IN202138004005.
IN Office Action dated Feb. 24, 2022 in Application No. IN202135037558.
IN Office Action dated Jul. 25, 2022, in Application No. IN202038028121.
IN Office Action dated Mar. 25, 2022, in Application No. IN202038028121.
IN Office Action dated Nov. 24, 2020 in IN Application No. 201737020192.
Indian Office Action dated Feb. 10, 2021 in IN Application No. 201837015533.
Indian Office Action dated Feb. 24, 2021 in IN Application No. 201737021981.
Indian Office Action dated Feb. 26, 2021 in IN Application No. 201837011989.
Indian Office Action dated Mar. 24, 2021 in IN Application No. 201817042545.
Indian Office Action dated Oct. 4, 2019 in IN Application No. 2514/KOLNP/2014.
Indian Office Action dated Sep. 25, 2020 in IN Application No. 201737018864.
International Preliminary Report on Patentability and written opinion dated Jul. 21, 2022 in Application PCT/US2021/012313.
International Preliminary Report on Patentability dated Mar. 3, 2022, in Application No. PCT/US2020/070427.
International Preliminary Report on Patentability dated Oct. 6, 2022 in PCT Application PCT/US2021/023433.
International Search Report and Written Opinion dated Aug. 2, 2022 in Application No. PCT/US2022/030757.
International Search Report and Written Opinion dated Aug. 22, 2022 in Application No. PCT/US2022/024343.
International Search Report and Written Opinion dated Mar. 25, 2022 in Application No. PCT/US2021/062774.
International Search Report and Written Opinion dated Sep. 1, 2022 in Application No. PCT/US2022/028850.
International Search Report and Written Opinion dated Sep. 26, 2022 in Application No. PCT/US2022/032993.
International Preliminary Report on Patentability dated Apr. 11, 2019 in PCT/US2017/052798.
International Preliminary Report on Patentability dated Apr. 18, 2019 in PCT Application No. PCT/US17/54120.
International Preliminary Report on Patentability dated Aug. 11, 2022 in PCT Application No. PCT/US2021/015378.
International Preliminary Report on Patentability dated Aug. 25, 2022, in PCT Application No. PCT/US2021/017946.

(56) References Cited

OTHER PUBLICATIONS

International Preliminary Report on Patentability dated Aug. 29, 2019 in PCT Application No. PCT/US2018/018241.
International Preliminary Report on Patentability dated Dec. 16, 2021, for International Application No. PCT/US2020/070123.
International Preliminary Report on Patentability dated Feb. 10, 2022 issued in Application No. PCT/US2020/044337.
International Preliminary Report on Patentability dated Feb. 19, 2015 issued in PCT/US2013/053625.
International Preliminary Report on Patentability dated Jan. 12, 2017 in PCT Application No. PCT/US15/38667.
International Preliminary Report on Patentability dated Jun. 13, 2019 in PCT Application No. PCT/US2017/061054.
International Preliminary Report on Patentability dated Jun. 22, 2017 in PCT Application No. PCT/US15/64555.
International Preliminary Report on Patentability dated Jun. 8, 2017 in PCT Application No. PCT/US2015/062387.
International Preliminary Report on Patentability dated Jun. 8, 2017 in PCT/US2015/062480.
International Preliminary Report on Patentability dated Mar. 29, 2018 in PCT Application No. PCT/US2016/052211.
International Preliminary Report on Patentability dated Mar. 7, 2019 in PCT/US2017/047664.
International Preliminary Report on Patentability dated May 1, 2014 in PCT/US2012/061137.
International Preliminary Report on Patentability dated May 11, 2018 in PCT/US2016/058872.
International Preliminary Report on Patentability dated Nov. 12, 2020 in PCT Application No. PCT/US2019/030467.
International Preliminary Report on Patentability dated Nov. 15, 2018 in PCT Application No. PCT/US201//031106.
International Preliminary Report on Patentability dated Nov. 18, 2021, issued in PCT/US2020/032269.
International Preliminary Report on Patentability dated Nov. 7, 2019 in PCT Application No. PCT/US2018/029406.
International Preliminary Report on Patentability dated Nov. 7, 2019 in PCT Application No. PCT/US2018/029460.
International Preliminary Report on Patentability dated Oct. 23, 2014 issued in PCT/US2013/036456.
International Preliminary Report on Patentability dated Oct. 29, 2020 in PCT/US2019/019455.
International Preliminary Report on Patentability dated Oct. 30, 2014 issued in PCT/US2013/034998.
International Preliminary Report on Patentability dated Oct. 30, 2014 issued in PCT/US2013/036235.
International Preliminary Report on Patentability dated Sep. 15, 2016 in Application No. PCT/US2015/019031.
International Preliminary Report on Patentability dated Sep. 24, 2020 in PCT/US2019/022129.
International Preliminary Report on Patentability dated Sep. 26, 2013, issued in PCT/US2012/027742.
International Preliminary Report on Patentability dated Sep. 26, 2013, issued in PCT/US2012/027828.
International Preliminary Report on Patentability dated Sep. 26, 2013, issued in PCT/US2012/027909.
International Search Report and Written Opinion dated Apr. 28, 2020 in PCT Application No. PCT/US2020/018677.
International Search Report and Written Opinion dated Aug. 8, 2022, in Application No. PCT/US2022/023605.
International Search Report and Written Opinion dated Dec. 26, 2013, issued in PCT/US2013/053625.
International Search Report and Written Opinion dated Feb. 15, 2016 in PCT/US2015/062480.
International Search Report and Written Opinion dated Jul. 6, 2022, in PCT Application No. PCT/US2022/020730.
International Search Report and Written Opinion dated Jul. 1, 2021 in PCT/US2021/021833.
International Search Report and Written Opinion dated Jul. 11, 2013, issued in PCT/US2013/034998.
International Search Report and Written Opinion dated Jul. 11, 2019 in PCT Application No. PCT/US2019/030467.
International Search Report and Written Opinion dated Jul. 23, 2013, issued in PCT/US2013/036235.
International Search Report and Written Opinion dated Jul. 26, 2013, issued in PCT/US2013/036456.
International Search Report and Written Opinion dated Jun. 23, 2021 in PCT Application No. PCT/US2021/015378.
International Search Report and Written Opinion dated Mar. 28, 2013 in PCT/US2012/061137.
International Search Report and Written Opinion dated Mar. 29, 2016 in PCT Application No. PCT/US15/64555.
International Search Report and Written Opinion dated May 26, 2014 in PCT/US2014/016974.
International Search Report and Written Opinion dated May 29, 2015 in Application No. PCT/US2015/019031.
International Search Report and Written Opinion dated Nov. 10, 2021 in PCT Application No. PCT/US2021/043143.
International Search Report and Written Opinion dated Nov. 16, 2018 in PCT Application No. PCT/US2018/029460.
International Search Report and Written Opinion dated Nov. 23, 2020 in PCT/US2020/070123.
International Search Report and Written Opinion dated Oct. 15, 2018 in PCT Application No. PCT/US2018/029406.
International Search Report and Written Opinion dated Oct. 16, 2014, issued in PCT/US2014/043514.
International Search Report and Written Opinion dated Oct. 16, 2015 in PCT Application No. PCT/US15/38667.
International Search Report and Written Opinion dated Sep. 1, 2022, in Application No. PCT/US2022/024812.
International Search Report and Written Opinion dated Sep. 24, 2012, issued in PCT/US2012/027742.
International Search Report and Written Opinion dated Sep. 24, 2012, issued in PCT/US2012/027909.
International Search Report and Written Opinion dated Sep. 26, 2012, issued in PCT/US2012/027828.
International Search Report and Written Opinion (ISA/EP) dated Dec. 7, 2020 in PCT Application No. PCT/US2020/032269.
International Search Report and Written Opinion (ISA/EP) dated May 9, 2019 in PCT/US2019/022129.
International Search Report and Written Opinion (ISA/KR) dated Apr. 2, 2018 in PCT Application No. PCT/US2017/061054.
International Search Report and Written Opinion (ISA/KR) dated Aug. 22, 2017 in PCT Application No. PCT/US2017/031106.
International Search Report and Written Opinion (ISA/KR) dated Aug. 5, 2021 in PCT Application No. PCT/US2021/027418.
International Search Report and Written Opinion (ISA/KR) dated Dec. 13, 2017 in PCT/US2017/047664.
International Search Report and Written Opinion (ISA/KR) dated Dec. 16, 2016 in PCT Application No. PCT/US2016/052211.
International Search Report and Written Opinion (ISA/KR) dated Feb. 3, 2017 in PCT/US2016/058872.
International Search Report and Written Opinion (ISA/KR) dated Feb. 6, 2018 in PCT/US2017/052798.
International Search Report and Written Opinion (ISA/KR) dated Jan. 9, 2018 in PCT Application No. PCT/US17/54120.
International Search Report and Written Opinion (ISA/KR) dated Jun. 14, 2019 in PCT/US2019/019455.
International Search Report and Written Opinion (ISA/KR) dated Mar. 8, 2016 in PCT Application No. PCT/US2015/062387.
International Search Report and Written Opinion (ISA/KR) dated May 23, 2018 in PCT Application No. PCT/US2018/018241.
Invitation to Pay Additional Fees dated Sep. 14, 2020 in PCT/US2020/070123.
Japanese Office Action dated Nov. 10, 2020 in JP Application No. 2018-521413.
JP Decision of Rejection dated Sep. 21, 2021, in application No. JP2018-521413.
JP Examination Report dated Nov. 26, 2020 in JP Application No. 2017-549175.
JP Office Action dated Dec. 7, 2021, in Application No. JP20170549175 with English translation.

(56) References Cited

OTHER PUBLICATIONS

JP Office Action dated Jul. 5, 2022, in Application No. JP2021-119155.
JP Office Action dated Jul. 20, 2021 in JP Application No. 2017-549175.
JP Office Action dated Jun. 16, 2020 in JP Application No. 2017-549175.
JP Office Action dated Mar. 1, 2022, in Application No. JP2020-175033 with translation.
JP Office Action dated Mar. 2, 2021 in JP Application No. 2018-557808.
JP Office Action dated Nov. 19, 2019 in JP Application No. 2017-549175.
JP office action dated Sep. 7, 2021, in JP Application No. 2020-175033.
Kipp & Zonen, "Solar Radiation" (known as of Sep. 3, 2014) [http://www.kippzonen.com/Knowledge-Center/Theoretical-info/Solar-Radiation].
Kleissl, Jan et al., "Recent Advances in Solar Variability Modeling and Solar Forecasting at UC San Diego," Proceedings, American Solar Energy Society, 2013 Solar Conference, Apr. 16-20, 2013, Baltimore, MD.
Korean Office Action dated Apr. 18, 2019 in KR Application No. 10-2014-7032108.
Korean Office Action dated Apr. 27, 2021 in KR Application No. 10-2021-7003065.
Korean Office Action dated May 25, 2020 in KR Application No. 10-2020-7005628.
KR Office Action dated Apr. 13, 2022, in KR Application No. KR1020217028044 with English translation.
KR Office Action dated Apr. 16, 2021 in KR Application No. 10-2018-7035235.
KR Office Action dated Dec. 22, 2021, in Application No. KR1020177018491 with English translation.
KR Office Action dated Feb. 22, 2022, in Application No. KR1020177017285.
KR Office Action dated Jan. 22, 2021 in KR Application No. 10-2016-7025862.
KR Office Action dated Jul. 31, 2021 in KR Application No. 10-2016-7025862.
KR Office Action dated May 28, 2022, in Application No. KR10-2022-7004024.
KR Office Action dated Oct. 26, 2021, in KR Application No. KR1020217028044 with English translation.
Letter dated Dec. 1, 2014 re Prior Art re U.S. Appl. No. 13/772,969 from Ryan D. Ricks representing MechoShade Systems, Inc.
Lim, Sunnie H.N. et al., "Modeling of optical and energy performance of tungsten-oxide-based electrochromic windows including their intermediate states," Solar Energy Materials & Solar Cells, vol. 108, Oct. 16, 2012, pp. 129-135.
Martel. S.J, et al., "Scientific Programming Lab Notes Lecture Notes", Department of Geology and Geophysics School of Ocean and Earth Science and Technology University of Hawai'i at Manoa, Sep. 2004, pp. 3.
Mumaw, R.J et al., "There is More to Monitoring a Nuclear Power Plant Than Meets the Eye", Human factors, 2000, vol. 42, No. 1, pp. 36-55.
NASA Tech Brief "Automated Power-Distribution System,", US Department of Commerce, Springfield, VA, Feb. 1991, p. 128 (2 pp).
National Aeronautics & Space Administration, "Cloud Radar System (CRS)," (known as of Sep. 3, 2014), published date of Jun. 16, 2014, [http://har.gsfc.nasa.gov/index.php?section=12].
National Aeronautics & Space Administration, "Cloud Remote Sensing and Modeling," (known as of Sep. 3, 2014), published date of Sep. 15, 2014, [http://atmospheres.gsfc.nasa.gov/climate/index.php?section=134].
"New from Pella: Windows with Smartphone-run blinds", Pella Corp., http://www.desmoinesregister.com/article/20120114/BUSINESS/301140031/0/biggame/?odyssey=nav%7Chead, Jan. 13, 2012.
Notice of Allowance dated Nov. 16, 2021 in U.S. Appl. No. 16/948,340.
Notice of Allowance dated Oct. 14, 2021 in U.S. Appl. No. 16/871,976.
Office Action dated Oct. 6, 2014 in U.S. Appl. No. 13/968,258.
"Ossia Wireless Charging", screenshot and picture of Cota device, accessed Apr. 20, 2015, 1 page.
Pasternack Enterprises, Inc. Technical Data Sheet for MCX Jack Connector Solder Attachment Surface Mount PCB (PE4889), 2013, 2 pp.
PCT Application No. PCT/US2021/021833 filed Mar. 11, 2021.
Preliminary Amendment dated Jan. 18, 2017 in U.S. Appl. No. 15/123,069.
Preliminary Amendment filed Jun. 12, 2019 for U.S. Appl. No. 15/882,719.
Preliminary Amendment filed Nov. 12, 2020 for U.S. Appl. No. 16/948,341.
Rajiv, "How does Cloud Radio Access Network (C-RAN) works," RF Page, Apr. 16, 2018, 5 pp. https://www.rfpage.com/how-cloud-radio-access-network-works/ Accessed May 19, 2021.
"Remote Radio Head for CPRI and 4G, 5G & LTE Networks," CableFree by Wireless Excellence Limited, 2020, 8 pp., https://www.cablefree.net/wirelesstechnology/4glte/remote-radio-head/ Accessed May 19, 2021.
"Remote Sensing: Clouds," Department of Atmospheric and Ocean Science, University of Maryland, (known as of Sep. 3, 2014) [http://www.atmos.umd.edu/~pinker/remote_sensing_clouds.htm].
Restriction requirement dated Oct. 18, 2021, for U.S. Appl. No. 16/849,540.
Rolith Inc., "NanoWeb: sub-micron transparent metal mesh conductors," [http://www.rolith.com/applications/transparent-conductive-electrodes] retrieved Jan. 29, 2016, 3 pp.
RU Office Action dated Sep. 24, 2018 in RU Application No. 2016139012.
Russian Office Action dated Nov. 15, 2017 in RU Application No. 2014145822.
Russian Office Action dated Jun. 27, 2017 in RU Application No. 2014145822.
Russian Office Action dated Jul. 10, 2019 in RU Application No. 2017123902.
Saad, A. "Printed millimeter-wave MIMO-based slot antenna arrays for 5G networks," AEU—International Journal of Electronics and Communications, vol. 99, Feb. 2019, pp. 59-69.
Saberin, J. R., "Optically Transparent Antennas for Small Satellites," University of Utah, Dept. of Electrical and Computer Engineering, Masters Thesis, Aug. 2010, 55 pp.
Science and Technology Facilities Council. "Cloud Radar: Predicting the Weather More Accurately." ScienceDaily, Oct. 1, 2008. [www.sciencedaily.com/releases/2008/09/080924085200.htm].
Sim, S., "Next generation data interchange: tool-to-tool application programming interfaces," IEEE Working Conference on Reverse Engineering, Nov. 25, 2000, pp. 278-280.
Singapore Notice of Eligibility for Grant & Search/Examination Report dated Sep. 15, 2015 in SG Application No. 11201406722V.
SunPartner Technologies web page, "Li-Fi", [http://sunpartnertechnologies.com/li-fi/]; 3 pages; retrieved Jan. 24, 2018.
SunPartner Technologies web page, "Smart Building-Cameleon", [http://sunpartnertechnologies.com/vitrage-intelligent/]; 3 pages; retrieved Jan. 24, 2018.
SunPartner Technologies web page, "Smart Building-Design Glass", [http://sunpartnertechnologies.com/vitrage-intelligent/]; 3 pages; retrieved Jan. 24, 2018.
SunPartner Technologies web page, "Smart Building-Vision Glass", [http://sunpartnertechnologies.com/vitrage-intelligent/]; 3 pages; retrieved Jan. 24, 2018.
SunPartner Technologies White Paper, "Wysips Connect, the first solution for the indoor/outdoor VLC lighting saturation problematics," Feb. 26, 2015, 6 pages, [http://sunpartnertechnologies.com/wp-content/uploads/2012/08/White_Paper_LiFi_26_02_2015.pdf].
Taiwan Office Action dated Dec. 31, 2020 issued in TW Application No. 106133563.
Taiwan Office Action dated Jan. 25, 2021 issued in TW Application No. 106128249.

(56) References Cited

OTHER PUBLICATIONS

Taiwanese First Office Action dated May 21, 2021 in TW 109134283.
Taiwanese Office Action dated Apr. 27, 2021 in TW Application No. 109138208.
Taiwanese Office Action dated Aug. 24, 2020 in TW Application No. 105134929.
Taiwanese Office Action dated Dec. 12, 2018 in TW Application No. 107129150.
Taiwanese Office Action dated Dec. 30, 2020 in TW Application No. 108114019.
Taiwanese Office Action dated Feb. 27, 2020 in TW Application No. 108126548.
Taiwanese Office Action dated Jul. 2, 2020 in TW Application No. 107119905.
Taiwanese Office Action dated Jul. 30, 2018 in TW Application No. 106137770.
Taiwanese Office Action dated Jun. 29, 2021 in TW Application No. 110115755.
Taiwanese Office Action dated Mar. 16, 2020 in TW Application No. 104139297.
Taiwanese Office Action dated Mar. 23, 2020 in TW Application No. 105130239.
Taiwanese Office Action dated Mar. 30, 2017 in TW Application No. 102113541.
Taiwanese Office Action dated May 13, 2019 in TW Application No. 104139217.
Taiwanese Office Action dated May 21, 2021 in TW Application No. 201833648.
Taiwanese Office Action dated Oct. 1, 2019 in TW Application No. 104139297.
"That's right, 5G could depend on Corning glass in your antenna," by Robert Triggs, Android Authority, Mar. 2, 2018, 5 pp . . . [https://www.androidauthority.com/corning-glass-5g-antenna-842341/] downloaded Nov. 13, 2018.
Third-Party Submission dated Feb. 2, 2015 and Feb. 18, 2015 PTO Notice re Third-Party Submission for U.S. Appl. No. 13/772,969.
TW Notice of Allowance & Search Report (translated) dated Jul. 30, 2021 in TW Application No. 106133985.
TW Office Action dated Jun. 6, 2022 in Application No. TW108115291 With English Translation.
TW Office Action dated Apr. 26, 2022 in Application No. TW110144841 with English translation.
TW Office Action dated Apr. 29, 2022, in Application No. TW110140314 with English translation.
TW office action dated Jan. 28, 2022, in Application No. TW107105853 with English Translation.
TW Office Action dated Jan. 28, 2022, in Application No. TW110109128 with English translation.
TW Office Action dated Jul. 14, 2022, in Application No. TW108121734 with English translation.
TW Office Action dated Jul. 28, 2022, in Application No. TW111124754 with English translation.
TW Office Action dated Mar. 13, 2022, in Application No. TW106114947 with English translation.
TW Office Action dated May 31, 2021 in TW Application No. TW 106114947.
TW Office Action dated Nov. 25, 2021, in Application No. TW110141330 with English translation.
TW Office Action dated Nov. 29, 2021, in Application No. TW109134283 with English translation.
U.S. Advisory Action dated Aug. 31, 2022 in U.S. Appl. No. 16/447,169.
U.S. Non-Final office Action dated Aug. 31, 2022 in U.S. Appl. No. 16/948,341.
U.S. Non-Final office Action dated Sep. 8, 2022 in U.S. Appl. No. 17/406,301.
U.S. Non-Final office Action dated Sep. 21, 2022 in U.S. Appl. No. 17/301,026.
U.S. Notice of Allowance dated May 12, 2022 in U.S. Appl. No. 17/171,667.
U.S. Notice of Allowance dated Sep. 8, 2022 in U.S. Appl. No. 16/946,140.
U.S. Appl. No. 62/988,861, inventors Khanna et al., filed Mar. 12, 2020.
U.S. Appl. No. 63/000,342, inventors Larson, filed Mar. 26, 2020.
U.S. Appl. No. 63/121,561, inventors Larson et al., filed Dec. 4, 2020.
U.S. Corrected Notice of Allowance dated Jun. 27, 2022 in U.S. Appl. No. 16/527,554.
U.S. Corrected Notice of Allowance dated Sep. 6, 2022 in U.S. Appl. No. 16/849,540.
U.S. Corrected Notice of Allowability dated Jan. 10, 2022, in U.S. Appl. No. 16/334,716.
U.S. Corrected Notice of Allowability dated Jun. 4, 2020 in U.S. Appl. No. 16/298,776.
U.S. Corrected Notice of Allowability dated May 3, 2021 in U.S. Appl. No. 16/253,971.
U.S. Corrected Notice of Allowability dated Nov. 1, 2019 in U.S. Appl. No. 15/334,835.
U.S. Corrected Notice of Allowability dated Sep. 23, 2021, in U.S. Appl. No. 16/338,403.
U.S. Corrected Notice of Allowability for U.S. Appl. No. 16/327,789 dated Mar. 1, 2021.
U.S. Corrected Notice of Allowance dated Apr. 26, 2022 in U.S. Appl. No. 16/334,716.
U.S. Corrected Notice of Allowance dated Apr. 28, 2022, in U.S. Appl. No. 15/733,765.
U.S. Corrected Notice of Allowance dated Aug. 19, 2021 in U.S. Appl. No. 16/871,976.
U.S. Corrected Notice of Allowance dated Feb. 28, 2022 in U.S. Appl. No. 16/486,113.
U.S. Corrected Notice of Allowance dated Jun. 3, 2022 In U.S. Appl. No. 16/849,540.
U.S. Final Office Action dated Apr. 30, 2012 in U.S. Appl. No. 13/049,750.
U.S. Final Office Action dated Aug. 19, 2013 in U.S. Appl. No. 13/049,756.
U.S. Final Office Action dated Dec. 23, 2020 in U.S. Appl. No. 16/338,403.
U.S. Final Office Action dated Feb. 26, 2015 in U.S. Appl. No. 13/479,137.
U.S. Final Office Action dated Feb. 6, 2020 in U.S. Appl. No. 16/451,784.
U.S. Final Office Action dated Jan. 11, 2019 in U.S. Appl. No. 15/334,835.
U.S. Final Office Action dated Jan. 27, 2014 in U.S. Appl. No. 13/479,137.
U.S. Final Office Action dated Jan. 31, 2019 in U.S. Appl. No. 15/534,175.
U.S. Final Office Action dated Jul. 1, 2019 in U.S. Appl. No. 15/334,832.
U.S. Final Office Action dated Jul. 2, 2015 in U.S. Appl. No. 13/049,756.
U.S. Final Office Action dated Jul. 2, 2019 in U.S. Appl. No. 15/691,468.
U.S. Final Office Action dated Jul. 3, 2019 in U.S. Appl. No. 15/623,237.
U.S. Final Office Action dated Jun. 24, 2022, in U.S. Appl. No. 16/447,169.
U.S. Final Office Action dated Mar. 15, 2018 in U.S. Appl. No. 14/951,410.
U.S. Final Office Action dated Mar. 17, 2017 in U.S. Appl. No. 14/887,178.
U.S. Final Office Action dated Mar. 18, 2020 in U.S. Appl. No. 16/253,971.
U.S. Final Office Action dated Mar. 3, 2020 in U.S. Appl. No. 16/508,099.
U.S. Final Office Action dated May 11, 2021 in U.S. Appl. No. 16/334,716.
U.S. Final Office Action dated May 15, 2014 in U.S. Appl. No. 13/449,251.
U.S. Final Office Action dated May 16, 2014 in U.S. Appl. No. 13/449,248.

(56) References Cited

OTHER PUBLICATIONS

U.S. Final Office Action dated Sep. 19, 2016 in U.S. Appl. No. 14/887,178.
U.S. Non Final Office Action dated Aug. 26, 2022 in U.S. Appl. No. 16/677,338.
U.S. Non Final Office Action dated Jan. 31, 2022 in U.S. Appl. No. 16/849,540.
U.S. Non Final office action dated Mar. 30, 2022, in U.S. Appl. No. 16/946,140.
U.S. Non-Final office Action dated Sep. 9, 2022 in U.S. Appl. No. 17/249,442.
U.S. Non-Final Office Action dated Aug. 12, 2022, in U.S. Appl. No. 16/655,032.
U.S. Non-Final Office Action dated Aug. 16, 2021 in U.S. Appl. No. 16/568,639.
U.S. Non-final Office Action dated Jul. 28, 2022 in U.S. Appl. No. 16/655,032.
U.S. Non-Final Office action dated Oct. 4, 2021, in U.S. Appl. No. 16/946,140.
U.S. Non-Final Office Action dated Oct. 28, 2021 in U.S. Appl. No. 15/733,765.
U.S. Non-Final Office Action dated Oct. 29, 2021 in U.S. Appl. No. 16/527,554.
U.S. Non-Final office Action dated Sep. 29, 2022 in U.S. Appl. No. 16/949,978.
U.S. Notice of Allowability (supplemental) dated Sep. 30, 2020 in U.S. Appl. No. 15/123,069.
U.S. Notice of Allowance (corrected) dated Apr. 18, 2019 in U.S. Appl. No. 15/320,725.
U.S. Notice of Allowance dated Apr. 13, 2015 in U.S. Appl. No. 14/657,380.
U.S. Notice of Allowance dated Apr. 17, 2019 in U.S. Appl. No. 15/534,175.
U.S. Notice of Allowance dated Apr. 17, 2019 in U.S. Appl. No. 15/910,936.
U.S. Notice of Allowance dated Apr. 19, 2021 in U.S. Appl. No. 16/099,424.
U.S. Notice of Allowance dated Apr. 26, 2019 for U.S. Appl. No. 15/365,685.
U.S. Notice of Allowance dated Apr. 6, 2020 in U.S. Appl. No. 16/298,776.
U.S. Notice of Allowance dated Apr. 6, 2022, in U.S. Appl. No. 15/733,765.
U.S. Notice of Allowance dated Apr. 9, 2020 in U.S. Appl. No. 15/123,069.
U.S. Notice of Allowance dated Dec. 13, 2018 in U.S. Appl. No. 15/978,029.
U.S. Notice of Allowance dated Dec. 14, 2018 in U.S. Appl. No. 15/910,936.
U.S. Notice of Allowance dated Dec. 22, 2021 in U.S. Appl. No. 16/334,716.
U.S. Notice of Allowance dated Dec. 27, 2021, in U.S. Appl. No. 16/568,639.
U.S. Notice of Allowance dated Dec. 31, 2020 in U.S. Appl. No. 16/523,624.
U.S. Notice of Allowance dated Dec. 31, 2020 in U.S. Appl. No. 16/555,377.
U.S. Notice of Allowance dated Dec. 7, 2020 in U.S. Appl. No. 16/508,099.
U.S. Notice of Allowance dated Feb. 11, 2022 in U.S. Appl. No. 16/486,113.
U.S. Notice of Allowance dated Feb. 16, 2022 in U.S. Appl. No. 16/664,089.
U.S. Notice of Allowance dated Feb. 24, 2020 for U.S. Appl. No. 16/295,142.
U.S. Notice of Allowance dated Feb. 4, 2021 in U.S. Appl. No. 16/253,971.
U.S. Notice of Allowance dated Jan. 10, 2014 in U.S. Appl. No. 13/449,235.
U.S. Notice of Allowance dated Jan. 22, 2015 in U.S. Appl. No. 13/682,618.
U.S. Notice of Allowance dated Jul. 1, 2020 in U.S. Appl. No. 15/334,832.
U.S. Notice of Allowance dated Jul. 1, 2020 in U.S. Appl. No. 15/623,237.
U.S. Notice of Allowance dated Jul. 15, 2020 in U.S. Appl. No. 15/882,719.
U.S. Notice of Allowance dated Jul. 15, 2021 in U.S. Appl. No. 16/871,976.
U.S. Notice of Allowance dated Jul. 17, 2019 in U.S. Appl. No. 15/123,069.
U.S. Notice of Allowance dated Jul. 17, 2019 in U.S. Appl. No. 15/320,725.
U.S. Notice of Allowance dated Jul. 20, 2012 in U.S. Appl. No. 13/049,623.
U.S. Notice of Allowance dated Jul. 25, 2019 in U.S. Appl. No. 15/534,175.
U.S. Notice of Allowance dated Jul. 29, 2020 for U.S. Appl. No. 16/439,376.
U.S. Notice of Allowance dated Jun. 8, 2022 in U.S. Appl. No. 15/733,765.
U.S. Notice of Allowance dated Jun. 14, 2021 in U.S. Appl. No. 16/338,403.
U.S. Notice of Allowance dated Jun. 17, 2014 in U.S. Appl. No. 13/309,990.
U.S. Notice of Allowance dated Jun. 20, 2022 in U.S. Appl. No. 16/527,554.
U.S. Notice of Allowance dated Jun. 26, 2019 in U.S. Appl. No. 15/334,835.
U.S. Notice of Allowance dated Mar. 10, 2021 in U.S. Appl. No. 15/691,468.
U.S. Notice of Allowance dated Mar. 20, 2019 in U.S. Appl. No. 15/320,725.
U.S. Notice of Allowance dated Mar. 26, 2021 in U.S. Appl. No. 16/254,434.
U.S. Notice of Allowance dated Mar. 9, 2018 in U.S. Appl. No. 14/887,178.
U.S. Notice of Allowance dated May 14, 2015 in U.S. Appl. No. 13/479,137.
U.S. Notice of Allowance dated May 14, 2019 in U.S. Appl. No. 15/623,235.
U.S. Notice of Allowance dated May 25, 2021 in U.S. Appl. No. 15/709,339.
U.S. Notice of Allowance dated May 26, 2020 in U.S. Appl. No. 16/451,784.
U.S. Notice of Allowance dated May 26, 2022, in U.S. Appl. No. 16/849,540.
U.S. Notice of Allowance dated May 6, 2020 in U.S. Appl. No. 15/623,237.
U.S. Notice of Allowance dated May 8, 2012 in U.S. Appl. No. 13/049,750.
U.S. Notice of Allowance dated Nov. 28, 2018 in U.S. Appl. No. 15/123,069.
U.S. Notice of Allowance dated Nov. 29, 2018 for U.S. Appl. No. 15/268,204.
U.S. Notice of Allowance dated Nov. 3, 2020 in U.S. Appl. No. 15/691,468.
U.S. Notice of Allowance dated Oct. 7, 2021 in U.S. Appl. No. 16/664,089.
U.S. Notice of Allowance dated Oct. 14, 2021 in U.S. Appl. No. 16/664,089.
U.S. Notice of Allowance dated Oct. 22, 2018 in U.S. Appl. No. 14/951,410.
U.S. Notice of Allowance dated Sep. 7, 2021 in U.S. Appl. No. 16/948,340.
U.S. Notice of Allowance dated Sep. 10, 2021, in the U.S. Appl. No. 15/709,339.
U.S. Notice of Allowance dated Sep. 16, 2021 in U.S. Appl. No. 16/948,340.
U.S. Notice of Allowance for U.S. Appl. No. 16/327,789 dated Feb. 4, 2021.

(56) References Cited

OTHER PUBLICATIONS

U.S. Notice of Allowance (supplemental) dated Jun. 12, 2015 in U.S. Appl. No. 13/479,137.
U.S. Office Action dated Apr. 27, 2018 in U.S. Appl. No. 15/123,069.
U.S. Office Action dated Apr. 6, 2018 for U.S. Appl. No. 15/268,204.
U.S. Office Action dated Aug. 21, 2019 in U.S. Appl. No. 16/508,099.
U.S. Office Action dated Aug. 22, 2019 in U.S. Appl. No. 16/298,776.
U.S. Office Action dated Aug. 7, 2018 in U.S. Appl. No. 15/910,936.
U.S. Office Action dated Aug. 7, 2019 for U.S. Appl. No. 16/295,142.
U.S. Office Action dated Aug. 7, 2020 in U.S. Appl. No. 16/338,403.
U.S. Office Action dated Dec. 10, 2020 in U.S. Appl. No. 16/871,976.
U.S. Office Action dated Dec. 24, 2013 in U.S. Appl. No. 13/309,990.
U.S. Office Action dated Dec. 31, 2018 in U.S. Appl. No. 15/334,832.
U.S. Office Action dated Feb. 21, 2020 in U.S. Appl. No. 15/334,832.
U.S. Office Action dated Feb. 23, 2016 in U.S. Appl. No. 13/449,248.
U.S. Office Action dated Feb. 24, 2015 in U.S. Appl. No. 14/163,026.
U.S. Office Action dated Feb. 3, 2012 in U.S. Appl. No. 13/049,750.
U.S. Office Action dated Feb. 4, 2019 in U.S. Appl. No. 15/623,235.
U.S. Office Action dated Feb. 7, 2019 in U.S. Appl. No. 15/623,237.
U.S. Office Action dated Feb. 7, 2019 in U.S. Appl. No. 15/691,468.
U.S. Office Action dated Jan. 16, 2015 in U.S. Appl. No. 14/468,778.
U.S. Office Action dated Jan. 16, 2020 in U.S. Appl. No. 15/529,677.
U.S. Office Action dated Jan. 18, 2013 in U.S. Appl. No. 13/049,756.
U.S. Office Action dated Jan. 21, 2021 in U.S. Appl. No. 15/709,339.
U.S. Office Action dated Jul. 21, 2020 in U.S. Appl. No. 16/523,624.
U.S. Office Action dated Jul. 21, 2020 in U.S. Appl. No. 16/555,377.
U.S. Office Action dated Jul. 23, 2020 in U.S. Appl. No. 16/508,099.
U.S. Office Action dated Jul. 24, 2018 in U.S. Appl. No. 15/978,029.
U.S. Office Action dated Jul. 25, 2019 in U.S. Appl. No. 16/253,971.
U.S. Office Action dated Jul. 25, 2019 in U.S. Appl. No. 15/529,677.
U.S. Office Action dated Jul. 29, 2020 in U.S. Appl. No. 16/253,971.
U.S. Office Action dated Jul. 3, 2014 in U.S. Appl. No. 13/479,137.
U.S. Office Action dated Jul. 6, 2018 in U.S. Appl. No. 15/534,175.
U.S. Office Action dated Jun. 3, 2015 in U.S. Appl. No. 13/449,251.
U.S. Office Action dated Mar. 12, 2020 in U.S. Appl. No. 15/882,719.
U.S. Office Action dated Mar. 15, 2019 in U.S. Appl. No. 15/334,835.
U.S. Office Action dated Mar. 16, 2020 for U.S. Appl. No. 16/439,376.
U.S. Office Action dated Mar. 25, 2016 in U.S. Appl. No. 14/887,178.
U.S. Office Action dated Mar. 27, 2012 in U.S. Appl. No. 13/049,623.
U.S. Office Action dated Mar. 27, 2018 in U.S. Appl. No. 15/334,835.
U.S. Office Action dated May 6, 2020 in U.S. Appl. No. 15/691,468.
U.S. Office Action dated Nov. 12, 2019 in U.S. Appl. No. 15/882,719.
U.S. Office Action dated Nov. 12, 2020 in U.S. Appl. No. 16/334,716.
U.S. Office Action dated Nov. 29, 2013 in U.S. Appl. No. 13/449,248.
U.S. Office Action dated Nov. 29, 2013 in U.S. Appl. No. 13/449,251.
U.S. Office Action dated Nov. 30, 2018 for U.S. Appl. No. 15/365,685.
U.S. Office Action dated Oct. 11, 2013 in U.S. Appl. No. 13/449,235.
U.S. Office Action dated Oct. 23, 2017 in U.S. Appl. No. 14/887,178.
U.S. Office Action dated Oct. 28, 2014 in U.S. Appl. No. 13/449,251.
U.S. Office Action dated Oct. 6, 2014 in U.S. Appl. No. 13/049,756.
U.S. Office Action dated Sep. 11, 2017 in U.S. Appl. No. 14/951,410.
U.S. Office Action dated Sep. 15, 2014 in U.S. Appl. No. 13/682,618.
U.S. Office Action dated Sep. 23, 2013 in U.S. Appl. No. 13/479,137.
U.S. Office Action dated Sep. 23, 2019 in U.S. Appl. No. 16/451,784.
U.S. Office Action dated Sep. 29, 2014 in U.S. Appl. No. 13/449,248.
U.S. Office Action dated Sep. 30, 2020 in U.S. Appl. No. 16/254,434.
U.S. Office Action dated Sep. 4, 2018 in U.S. Appl. No. 15/320,725.
U.S. Office Action for U.S. Appl. No. 16/327,789 dated Sep. 28, 2020.
U.S. Appl. No. 16/338,403, inventors Shrivastava et al., filed Mar. 29, 2019.
U.S. Appl. No. 16/696,887, inventors Brown et al., filed Nov. 26, 2019.
U.S. Appl. No. 62/102,515, inventors Nagar et al., filed Jan. 12, 2015.
U.S. Appl. No. 62/102,516, inventors Nagar et al., filed Jan. 12, 2015.
U.S. Appl. No. 63/187,632, inventors Hur et al., filed May 12, 2021.
U.S. Appl. No. 63/226,127, inventors Lee et al., filed Jul. 21, 2021.
U.S. Pat. Appl. No. PCT/US2021/027418, inventors Makker et al., filed on Apr. 15, 2021.
U.S. Appl. No. 17/759,709, Inventors Trikha et al., filed Jul. 28, 2022.
U.S. Appl. No. 17/791,507, inventors Gopinathanasari et al., filed Jul. 7, 2022.
U.S. Appl. No. 17/814,427, inventors Martinson et al., filed Jul. 22, 2022.
U.S. Appl. No. 17/869,725, inventors Shrivastava et al., filed Jul. 20, 2022.
U.S. Appl. No. 17/904,156, inventors Brown et al., filed Aug. 12, 2022.
U.S. Appl. No. 17/909,925, inventors Vangati et al., filed Sep. 7, 2022.
U.S. Appl. No. 17/910,722, inventor Trikha et al., filed Sep. 9, 2022.
U.S. Appl. No. 17/940,951, inventors Vangati et al., filed Sep. 8, 2022.
U.S. Preliminary Amendment dated Dec. 31, 2019 in U.S. Appl. No. 16/608,159.
U.S. Appl. No. 63/080,899, inventor Makker et al., filed Sep. 21, 2020.
US PTAB Decision on Appeal dated Feb. 25, 2019 in U.S. Appl. No. 13/449,248.
US PTAB Decision on Appeal dated Feb. 25, 2019 in U.S. Appl. No. 13/449,251.
U.S. Supplemental Notice of Allowability dated Aug. 6, 2020 in U.S. Appl. No. 15/334,832.
U.S. Supplemental Notice of Allowance dated Aug. 1, 2022 in U.S. Appl. No. 17/171,667.
U.S. Supplementary Notice of Allowability dated Dec. 30, 2021, in U.S. Appl. No. 16/948,340.
View Inc., Installation Description, Tintable Electrochromic Windows and an Associated Power Distribution Network, prior to Sep. 2014 (3 pages).
Vinci Construction Datasheet for "Horizon-Solar Connected Window", Dec. 2016 (2 pp).
WeBoost Connect 3G Cell Phone Booster 472205 [https://store.weboost.com/products/connect-3g-directional] retrieved Apr. 1, 2016, 12 pp.
Woods, D., "The Alarm Problem and Directed Attention in Dynamic Fault Management.", Ergonomics, 1995, vol. 38, No. 11, pp. 2371-2393.
Yasin, T. et al., "A study on the efficiency of transparent patch antennas designed from conductive oxide films," IEEE International Symposium on Antennas and Propagation (APSURSI), Spokane, WA, Jul. 3-8, 2011, pp. 3085-3087.
Yasin, T., "Transparent antennas for solar cell integration," Utah State University, Dept. of Electrical Engineering, Doctoral Thesis, 2013, 98 pp.
CN Office Action dated Mar. 2, 2022 in Application No. CN201980042340.1 with English translation.
Density DPU Technical Specifications v1.0, Density, 2018, downloaded from www.density.io.
Dols, W. Stuart, et al., A tool to model the fate and transport of indoor microbiological aerosols (FaTIMA), NIST Technical Note 2095, National Institute of Standards and Technology, US Department of Commerce, Jun. 2020, 32 pp. https://doi.org/10.6028/NIST.TN.2095.
EP Office action dated Jan. 10, 2022, in Application No. EP19745809.4.
"Halio Rooftop Sensor Kit (Model SR500)," Product Data Sheet, Kinestral Technologies, 2020, 4 pp.
International Preliminary Report on Patentability dated Dec. 9, 2021, in PCT Application No. PCT/US2020/035485.
International Preliminary Report on Patentability dated Dec. 22, 2020 in PCT/US2019/038429.
International Search Report and Written Opinion dated Sep. 16, 2019 in PCT/US2019/038429.
International Search Report and Written Opinion (ISA/EP) dated Sep. 30, 2020 in PCT Application No. PCT/US2020/035485.
Joseph, J., "Xiaomi shows off near perfect Under Screen Camera Technology," Gizchina.com, Aug. 28, 2020, 7 pp., https://www.

(56) References Cited

OTHER PUBLICATIONS gizmochina.com/2020/08/28/xiaomi-perfected-third-gen-under-screen-camera-technology-prototype/, retrieved Apr. 21, 2021.
PCT Application No. PCT/US2021/012313 filed Jan. 6, 2021.
PCT Application No. PCT/US2021/015378 filed Jan. 28, 2021.
PCT Application No. PCT/US2021/023433 filed Mar. 23, 2021.
PCT Application No. PCT/US2021/030798 filed May 5, 2021.
PCT Application No. PCT/US2021/052587 filed Sep. 29, 2021.
"SPN1 Sunshine Pyranometer," Product Overview, Specification, Accessories and Product Resources, Delta-T Devices, May 5, 2016, 9 pp. https://www.delta-t.co.uk/product/spn1/ (downloaded Apr. 28, 2020).
TW Office Action dated Mar. 15, 2022, in Application No. TW109112242 with English translation.
U.S. Advisory Action dated Dec. 15, 2021 in U.S. Appl. No. 16/447,169.
U.S. Appl. No. 17/612,479, inventors Rozbicki et al., filed Nov. 18, 2021.
U.S. Appl. No. 62/958,653, inventors Gopinathanasari et al., filed Jan. 8, 2020.
U.S. Appl. No. 62/993,617, inventors Gupta et al., filed Mar. 23, 2020.
U.S. Appl. No. 63/020,819, inventors Gupta et al., filed May 6, 2020.
U.S. Appl. No. 63/029,301, inventors Gupta et al., filed May 22, 2020.
U.S. Appl. No. 63/033,474, inventors Gupta et al., filed Jun. 2, 2020.
U.S. Appl. No. 63/034,792, inventors Gupta et al., filed Jun. 4, 2020.
U.S. Appl. No. 63/041,002, inventors Gupta et al., filed Jun. 18, 2020.
U.S. Appl. No. 63/057,120, Inventors Gupta et al., filed Jul. 27, 2020.
U.S. Appl. No. 63/069,358, inventors Gupta et al., filed Aug. 24, 2020.
U.S. Appl. No. 63/078,805, Inventors Gupta et al., filed Sep. 15, 2020.
U.S. Appl. No. 63/079,851, inventors Gupta et al., filed Sep. 17, 2020.
U.S. Appl. No. 63/106,058, inventors Rasmus-Vorrath et al., filed Oct. 27, 2020.
U.S. Appl. No. 63/115,886, Inventors Gupta et al., filed Nov. 19, 2020.
U.S. Appl. No. 63/133,725, inventors Gopinathanasari et al., filed Jan. 4, 2021.
U.S. Appl. No. 63/159,814, Inventors Gupta et al., filed Mar. 11, 2021.
U.S. Appl. No. 63/173,759, inventors Rasmus-Vorrath et al., filed Apr. 12, 2021.
U.S. Appl. No. 63/209,362, Inventors Gomez-Martinez et al., filed Jun. 10, 2021.
U.S. Appl. No. 63/233,122, inventors Gupta et al., filed Aug. 13, 2021.
U.S. Final Office Action dated Aug. 13, 2021 in U.S. Appl. No. 16/447,169.
U.S. Final Office Action dated Jan. 1, 2021 in U.S. Appl. No. 16/550,052.
U.S. Final Office Action dated Oct. 28, 2021 in U.S. Appl. No. 16/550,052.
U.S. Non-Final Office Action dated Mar. 25, 2022, in U.S. Appl. No. 16/550,052.
U.S. Office Action dated Jan. 25, 2021 in U.S. Appl. No. 16/447,169.
U.S. Office Action dated May 5, 2021 in U.S. Appl. No. 16/550,052.
U.S. Office Action dated Sep. 18, 2020 in U.S. Appl. No. 16/550,052.
U.S. Appl. No. 63/124,673, inventors Tai et al., filed Dec. 11, 2020.
U.S. Appl. No. 63/146,365, inventors Brown et al., filed Feb. 5, 2021.
U.S. Appl. No. 63/163,305, inventors Trikha et al., filed Mar. 19, 2021.
U.S. Appl. No. 63/171,871, inventors Gomez-Martinez et al., filed Apr. 7, 2021.
U.S. Appl. No. 63/181,648, inventors Makker et al., filed Apr. 29, 2021.
U.S. Pat. Appl. No. PCT/US2021/017946, filed on Feb. 12, 2021.
U.S. Appl. No. 63/212,483, inventors Martinson et al., filed Jun. 18, 2021.
U.S. Appl. No. 63/246,770, Inventors Martinson et al., filed Sep. 21, 2021.
U.S. Preliminary Amendment dated Apr. 6, 2020 in U.S. Appl. No. 16/550,052.
U.S. Preliminary Amendment dated Nov. 13, 2019 in U.S. Appl. No. 16/447,169.
CN Office Action dated Nov. 2, 2022, in Application No.CN201980042340.1.
International Preliminary Report on Patentability dated Dec. 1, 2022, in PCT Application No. PCT/US2021/033544.
International Search Report and Written Opinion dated Sep. 3, 2021 in PCT Application No. PCT/US2021/033544.
JP Office Action dated Dec. 20, 2022 in JP Application No. JP2020-570981.
U.S. Final Office Action dated Dec. 2, 2022 in U.S. Appl. No. 16/550,052.
U.S. Non-Final office Action dated Nov. 15, 2022 in U.S. Appl. No. 16/447,169.
U.S. Appl. No. 17/924,105, inventors et al., filed Nov. 8, 2022.

\* cited by examiner

SYSTEMS AND METHODS FOR MANAGING BUILDING WELLNESS

CROSS-REFERENCE TO RELATED APPLICATION

This application claims priority to and the benefit of U.S. Provisional Patent Application No. 63/030,507 filed on May 27, 2020, the disclosure of which is incorporated herein by reference in its entirety.

FIELD OF THE INVENTION

The present invention relates to systems and methods for managing building wellness.

BACKGROUND OF THE INVENTION

Information about building wellness is essential in a world struggling to manage and recover from the global pandemic caused by COVID-19. Such information is critical for tenants to: (i) ensure a healthy environment for employees, so they are productive and feel safe in the office; (ii) respond quickly to crises with staffing processes and policies for protecting employee safety and ensuring business continuity; and (iii) understand building and space performance for real estate leases. Building wellness information is also critical for employees to (i) manage personal safety when planning trips to and from the office, and (ii) enjoy a sense of comfort and safety in knowing that the environmental and wellness conditions of the office are being rigorously monitored.

SUMMARY OF THE INVENTION

In various examples, the systems and methods described herein can be used to obtain and process wellness-related data for a building for the purpose of calculating a wellness index (alternatively referred to as a health index) for the building. The wellness-related data can be or include one or more wellness parameters related to, for example, air and water quality, occupancy, body temperature, reported illnesses, and/or previous building maintenance or cleaning. In general, the wellness index provides an overall measure or indication of a wellness of the building. The wellness index can indicate, for example, how risky it may be from a personal wellness standpoint for a person to enter or spend time in the building. For example, the wellness index can indicate a likelihood that the building may be contaminated with a virus (e.g., a coronavirus) or other pathogen. Additionally, or alternatively, the wellness index can provide an indication of how likely it may be that a person who enters or spends time in the building will be exposed to a virus or other pathogen.

In some implementations, the wellness index and/or supporting data can be made available to one or more occupants of the building (e.g., employees) or people who otherwise visit or enter the building (e.g., vendors, customers, etc.). Such information can be made available through a software application (e.g., installed on user mobile phones, personal computers, etc.), digital signage, text messaging or notifications, a tenant interface, and/or building manager tools. Availability of the wellness index and related data can empower occupants and building staff to make data-driven decisions around managing staff and resources in the context of any wellness risks associated with conditions in the building. For example, the wellness index can be used to facilitate a corrective action to improve the current wellness index or building wellness. Such action can be or include, for example, requiring people to vacate the building or move to specific portions of the building, requiring people to reduce occupancy in the building, requiring use of personal protective equipment, and/or performing maintenance or cleaning on one or more contaminated or damaged building components or areas.

In various examples, the wellness parameters used to calculate the wellness index for a building can include data related to a condition of the building and/or the building's occupants or visitors. The wellness parameters can include, for example, building occupancy data (e.g., a number of occupants and/or a population density for the building), occupant wellness report data (e.g., data indicating one or more occupants is presently sick or recovering from recent illness), air quality data, water quality data (e.g., data describing water quality for a cooling tower), building cleanliness data (e.g., a length of time since a previous deep cleaning or recent pathogen exposure), occupant body temperature data, historical building wellness index data (e.g., a rate of change or trend for the wellness index), or any combination thereof. Such data can be collected or obtained from one or more building managers, occupants, medical professionals, cleaning professionals, other personnel, or measurement devices.

The wellness index can be calculated by combining one or more of the wellness parameters. For example, each wellness parameter can be assigned a numerical value (e.g., from 0 to 1, or from −1 to 1) indicating a wellness risk associated with the parameter. For example, if a parameter indicates a wellness risk is high, the value of the parameter can be set to 0 or −1. Alternatively, if the parameter indicates the wellness risk is low, the value of the parameter can be set to 1. Each wellness parameter can then be assigned a weight, and the wellness index can be calculated as follows:

$$\text{Wellness Index} = W_1P_1 + W_2P_2 + \ldots + W_NP_N \quad (1)$$

where $P_i$ is a wellness parameter, $W_i$ is a corresponding weight, and N is the number of wellness parameters. Other methods for calculating the wellness index are contemplated. For example, one or more machine learning models or classifiers can be trained and used to calculate the wellness index. For example, one or more wellness parameters can be provided to a machine learning model as input, and the wellness index can be provided by the machine learning model as output. The machine learning model can be trained to identify building wellness issues using training data that includes, for example, wellness parameters and corresponding values for the wellness index. Additionally, or alternatively, one or more functional forms can be used to combine the wellness parameters (e.g., besides the linear form in equation (1)) and calculate the wellness index. Such functional forms can be or include, for example, non-linear functions, exponential functions, logarithmic functions, quadratic functions, and the like.

Advantageously, the systems and methods described herein can improve accuracy and/or automation of data processing. Data related to building wellness is collected from a variety of sources, including sensors in and around buildings (e.g., body temperature scanners, air quality sensors, security cameras, occupancy sensors, social distancing badges, etc.), push buttons, medical testing labs, and/or information provided by occupants (e.g., through surveys or self-reporting). The systems and methods can aggregate such data in an automated manner to calculate a building wellness index and take corrective action, as needed. Compared to prior approaches, which can rely on manual data collection and analysis, the computer-implemented systems, connected sensors, algorithms, and machine learning techniques described herein are able to achieve a more automated approach for processing data related to building wellness and ensuring that issues related to building wellness are identified and addressed in an efficient and accurate manner.

In a first aspect, the invention relates to a computer-implemented method of managing building wellness. In some embodiments, the method includes the steps of: obtaining wellness parameters for a building (e.g., an office building) having an occupant(s) (e.g., an employee(s)); processing the wellness parameters to determine a current wellness index for the building; and, based on the current wellness index, and sending a message regarding the current wellness index to a recipient(s) (e.g., a building occupant), (ii) displaying the current wellness index for a user(s), and/or identifying a remediation action(s) to improve the current wellness index. In some variations, the wellness parameters may include building occupancy data, occupant wellness report data, air quality data, water quality data, building cleanliness data, occupant body temperature data, historical building wellness index data, and/or any combination thereof. The current wellness index provides an indication of a risk of being exposed to a pathogen (e.g., a virus) inside the building.

In some implementations, the method may include one or more of the following: building occupancy data may include a number of occupants for the building and/or a population density for the building; occupant wellness report data may include data indicating an occupant(s) is presently sick or recovering from recent illness; water quality data may include data describing water quality for a cooling tower; building cleanliness data may include a length of time since a previous deep cleaning or recent pathogen exposure; historical building wellness index data comprises at least one of a rate of change for the wellness index or a trend for the wellness index.

In some applications, displaying the current wellness index may include presenting the current wellness index on a client device of a user(s) and/or identifying a remediation action(s) may include instructing people to vacate the building, move to a specific portion of the building, use personal protective equipment inside the building, and/or clean an area(s) of the building.

In a second aspect, the invention relates to a system for managing building wellness. In some embodiments, the system includes a computer processor(s) adapted to perform operations. In some embodiments, stored instructions in the computer processor(s) include: obtaining wellness parameters for a building (e.g., an office building) having an occupant(s) (e.g., an employee(s)); processing the wellness parameters to determine a current wellness index for the building; and, based on the current wellness index, sending a message including the current wellness index to a recipient(s) (e.g., an occupant(s), displaying the current wellness index for a user(s), and/or identifying a remediation action(s) to improve the current wellness index. In some variations, the wellness parameters may include building occupancy data, occupant wellness report data, air quality data, water quality data, building cleanliness data, occupant body temperature data, historical building wellness index data, and/or any combination thereof. The current wellness index provides an indication of a risk of being exposed to a pathogen (e.g., a virus) inside the building.

In some implementations, building occupancy data may include a number of occupants for the building and/or a population density for the building; occupant wellness report data may include data indicating an occupant(s) is presently sick or recovering from recent illness; water quality data may include data describing water quality for a cooling tower; building cleanliness data may include a length of time since a previous deep cleaning or recent pathogen exposure; historical building wellness index data may include a rate of change for the wellness index and/or a trend for the wellness index.

In some applications, displaying the current wellness index may include presenting the current wellness index on a client device of a user(s) and/or identifying the remediation action(s) may include instructing people to vacate the building, move to a specific portion of the building, use personal protective equipment inside the building, and/or clean an area(s) of the building.

In a third aspect, the invention relates to a non-transitory computer-readable medium having instructions stored thereon that, when executed by a computer processor(s), cause the computer processor(s) to perform operations. In some embodiments, the stored instructions include: obtaining wellness parameters for a building (e.g., an office building) having an occupant(s) (e.g., an employee(s)); processing the wellness parameters to determine a current wellness index for the building; and, based on the current wellness index, sending a message including the current wellness index to a recipient(s) (e.g., an occupant(s), displaying the current wellness index for a user(s), or identifying a remediation action(s) to improve the current wellness index. In some variations, the wellness parameters may include building occupancy data, occupant wellness report data, air quality data, water quality data, building cleanliness data, occupant body temperature data, historical building wellness index data, and/or any combination thereof. The current wellness index provides an indication of a risk of being exposed to a pathogen (e.g., a virus) inside the building.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which.

DETAILED DESCRIPTION

Terminology

Figure 1:
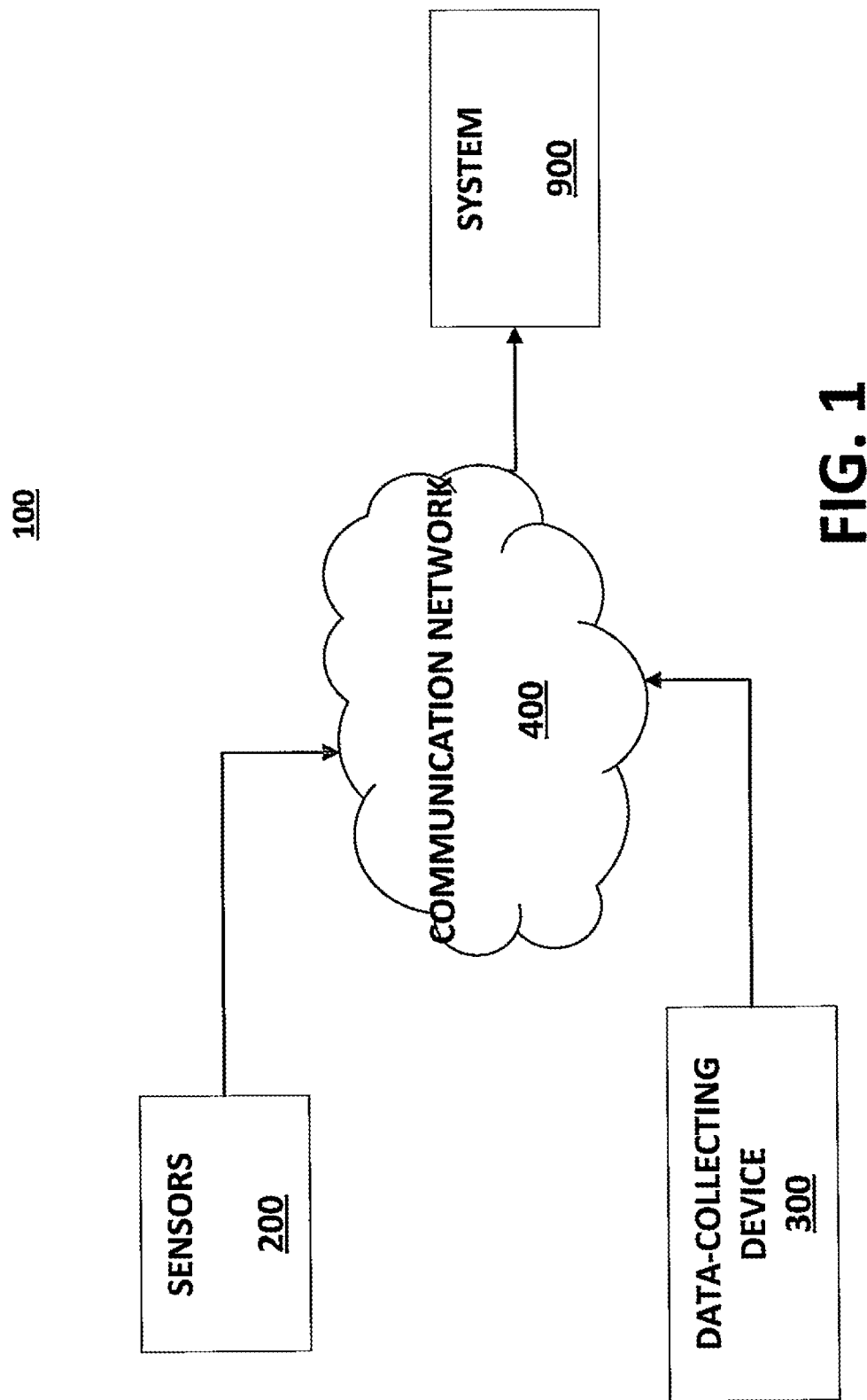
FIG. 1 shows a block diagram of an exemplary architecture for managing building wellness, in accordance with some embodiments of the present invention.

The phraseology and terminology used herein is for the purpose of description and should not be regarded as limiting.

The term "approximately", the phrase "approximately equal to", and other similar phrases, as used in the specification and the claims (e.g., "X has a value of approximately Y" or "X is approximately equal to Y"), should be understood to mean that one value (X) is within a predetermined range of another value (Y). The predetermined range may be plus or minus 20%, 10%, 5%, 3%, 1%, 0.1%, or less than 0.1%, unless otherwise indicated.

Measurements, sizes, amounts, etc. may be presented herein in a range format. The description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as 10-20 inches should be considered to have specifically disclosed subranges such as 10-11 inches, 10-12 inches, 10-13 inches, 10-14 inches, 11-12 inches, 11-13 inches, etc.

The indefinite articles "a" and "an," as used in the specification and in the claims, unless clearly indicated to the contrary, should be understood to mean "at least one." The phrase "and/or," as used in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The use of "including," "comprising," "having," "containing," "involving," and variations thereof, is meant to encompass the items listed thereafter and additional items.

Use of ordinal terms such as "first," "second," "third," etc., in the claims to modify a claim element does not by itself connote any priority, precedence, or order of one claim element over another or the temporal order in which acts of a method are performed. Ordinal terms are used merely as labels to distinguish one claim element having a certain name from another element having a same name (but for use of the ordinal term), to distinguish the claim elements.

Building Wellness Index

Advantageously, the systems and methods described herein are structured and arranged to calculate a building wellness index (BWI) providing a plurality (e.g., four) wellness levels termed "good," "moderate," "use caution," and "alert." Those of ordinary skill in the art can appreciate that the number and names of the wellness levels may vary by implementation and that the following description is meant to be instructive and illustrative of the BWI. In calculating a BWI, assumptions and considerations may include the desire to avoid (i) recommendations that violate any lease and (ii) claims that may directly impact personal and/or individual health decisions. Moreover, the BWI calculated should be (i) based on governmental guidelines when determining any occupancy thresholds and (ii) based on established (e.g., ASHRAE, CDC, EPA, and the like) baselines for any thresholds relating to health and wellness. Furthermore, although all data will be available for use in calculating the BWI, not all data may factor into the risk level calculation.

When the data used to calculate a BWI results in a "good" level, there is deemed no increased health risk to occupants (e.g., tenants, building employees, building visitors, and so forth); hence, occupants are free to enter into and work freely within the building without the need for wearing increased personal protection equipment (PPE), social distancing, or other restrictive practices. Alternatively, when the data used to calculate a BWI results in an "alert" level, conditions within the building are deemed life threatening or, in the alternative, the building must comply with a government "shelter in place" order. Under "alert" conditions, potential occupants (e.g., tenants, building employees, building visitors, and so forth) should avoid coming to the office building and should work from home. The intermediate alert levels stand somewhere between the ideal conditions of "good" and the heightened risk conditions of "alert." Thus, the "moderate" and "use caution" levels reflect a decrease in life threatening conditions and/or government restrictions, resulting in a corresponding decrease in usage limitations and required safety practices for occupants.

In calculating a BWI risk rating, direct, indirect, and other factors may be taken into account. As previously stated, although all data will be available for use in calculating the BWI, not all data may factor into the risk level calculation. Direct factors include data that are direct indicators of a possible risk due to a pathogen (e.g., a virus, such as COVID-19) and are primary contributors to risk level escalation. Indirect factors may indicate overall risk trends or otherwise contribute to possible risk due to a pathogen (e.g., a virus, such as COVID-19) and a secondary contributor(s) to risk level escalation. Other factors that are neither direct nor indirect may have no correlation to possible risk due to a pathogen (e.g., a virus, such as COVID-19); however, they are important to overall wellness and health of building occupants.

Table I provides exemplary risk rate criteria due to direct factors for each of the four wellness levels. In some implementations, these factors may include historic risk, building density, pathogen (e.g., COVID) space testing, reported pathogen (e.g., COVID) cases, and elevated employee temperatures.

TABLE I

LEVEL CRITERIA (DIRECT FACTORS)

| FACTOR | ALERT IF ANY OF THE FOLLOWING ARE TRUE | USE CAUTION IF ANY OF THE FOLLOWING ARE TRUE | MODERATE IF ANY OF THE FOLLOWING ARE TRUE | GOOD IF ALL OF THE FOLLOWING ARE TRUE |
|---|---|---|---|---|
| Historic Risk | N/A | 24 hours < since "ALERT" status | 24 hours < since "USE CAUTION" status | >24 hours since "MODERATE" status |
| Building Density | "shelter in place" or "stay at home" order from CDC or government agency | Building density < 110% of target and government agency recommendation in effect | Building density > 110% of target and government agency recommendation in effect | No government agency recommendation in effect |
| Pathogen (COVID) Space Testing | | 3 samples < detected in the last week | Between 1 and 3 samples detected in the last week | More than one week since last sample was discovered. |
| Reported Pathogen (COVID) Cases | | 1% of building population < reported with pathogen in last 2 weeks | 1 or more cases of pathogen reported in the last two weeks | No cases of highly infectious diseases reported in the last two weeks |
| Elevated Employee Temperatures | | 1 standard deviation < above monthly average baseline | | Monthly average baseline of elevated temperature employees≤ |

Table II provides exemplary risk rate criteria due to other factors for each of the four levels. In some implementations, these factors may include carbon monoxide (CO) levels, levels of particulate matter (PM10), ozone levels, volatile organic compounds (VOC) levels, formaldehyde levels, and legionella levels (for buildings that draw potable water from cooling water towers). The Table II factors deal more with the environment and how it may affect human beings as opposed to factors that affect the building itself.

TABLE II

LEVEL CRITERIA (OTHER FACTORS)

| FACTOR | ALERT IF ANY OF THE FOLLOWING ARE TRUE | USE CAUTION IF ANY THREE (3) OF THE FOLLOWING ARE TRUE | MODERATE IF ANY THREE (3) OF THE FOLLOWING ARE TRUE | GOOD |
|---|---|---|---|---|
| CO (in 8 hours) | ≥12.4 ppm | 9.5 < ≤12.4 ppm | 4.4 ppm < ≤9.4 ppm | |
| PM 10 (in 24 hours) | >255 µg/m³ | 155 µg/m³ < ≤254 µg/m³ | 54 µg/m³ < ≤154 µg/m³ | |
| OZONE (in 8 hours) | 0.086 ppm < ≤0.105 ppm | 0.070 ppm < ≤0.086 ppm | 0.054 ppm < ≤0.070 ppm | |
| VOC | >1000 µg/m³ | 500 µg/m³ < ≤100 µg/m³ | 500 µg/m³< | |
| Formaldehyde | ≥5 ppm (in 8 hours) | | 0.027 ppm< | |
| Legionella | YES | | | NO |

Table III provides exemplary risk rate criteria due to indirect factors for each of the four levels. These indirect factors may include, for example, carbon dioxide levels ($CO_2$), humidity, levels of particulate matter (PM2-5), and employee absenteeism. The Table III factors deal more with the environment and how it may affect human beings.

TABLE III

| | LEVEL CRITERIA (INDIRECT FACTORS) | | | |
|---|---|---|---|---|
| FACTOR | ALERT IF ANY OF THE FOLLOWING ARE TRUE | USE CAUTION IF ANY OF THE FOLLOWING ARE TRUE | MODERATE IF ANY OF THE FOLLOWING ARE TRUE | GOOD IF ANY OF THE FOLLOWING ARE TRUE |
| $CO_2$ | | | >10% above (ambient) outside air $CO_2$ levels | <10% below (ambient) outside air $CO_2$ levels |
| Humidity | | | <40% | 40% < <60% |
| PM2-5 (in 24 hours) | >55.4 µg/m$^3$ | 35.4 µg/m$^3$ < ≤55.4 µg/m$^3$ | | ≤35.4 µg/m$^3$ |
| Employee Absenteeism | | | Illness-related employee absenteeism has trended upward for 3 days | Illness-related employee absenteeism has remained stable or decreased for at least 3 days |

System Architecture

Referring to FIG. 1, an exemplary architecture of an embodiment of a system 100 for managing building wellness is shown. In some implementations, the system 100 includes a plurality of sensors 200 and/or data-collecting devices 300, as well as a computer-based system 900 that is configured to calculate a wellness (or health) index using, inter alia, data from the plurality of sensors 200 and/or data-collecting devices 300. Although the term "devices" connotes a mechanical means, those of ordinary skill in the art can appreciate that "devices" may also include a survey, a questionnaire, computer input, and so forth.

A communication network 400 enables the transfer of (e.g., communication) signals and data between the computer-based system 900 and the sensors 200 and data-collecting devices 300, such that data collected by the sensors 200 and data-collecting devices 300 may provide insight as to what is occurring, what may be occurring, and/or what is likely to occur within the (e.g., office) building. Moreover, these data and insights may be used so that remedial, preventive, and/or other action may be taken to improve the quality of life within the building. In some variations, such action may be communicated (e.g., via email, text message, phone call, and the like) to individuals or building departments responsible for effecting the remedial action.

In some embodiments, the computer-based system 900 includes stored instructions for operations that, initially, may include obtaining wellness parameters for a (e.g., office) building having occupants (e.g., employees and/or visitors). Wellness parameters may include, for the purpose of illustration rather than limitation: building occupancy data, occupant wellness report data, air quality data, water quality data, building cleanliness data, occupant body temperature data, historical building wellness index data, and/or any combination thereof. Building occupancy data may include a number of occupants for the building, which can include a floor-by-floor and a room-by-room assessment and/or a population density for the building. Occupant wellness report data may include data indicating one or more occupants is presently sick or recovering from recent illness. Water quality data may include data describing water quality for a cooling tower. Building cleanliness data may include a length of time since a previous deep cleaning or recent pathogen exposure. Historical building wellness index data may include a rate of change for the wellness index and/or a trend for the wellness index.

The computer-based system 900 may also include stored instructions for processing the wellness parameters to determine a current wellness (or health) index for the building as indicia of the risk of being exposed to a pathogen (e.g., a virus, COVID-19, and so forth); and, based on the current wellness index, sending a message to a recipient who is designated to take some action to address a deficiency in the current wellness index. For example, sending a message may include sending the current wellness index to a recipient(s), displaying the current wellness index for a user(s), and/or identifying a remediation action(s) to improve the current wellness index. The current wellness index provides an indication of a risk of being exposed to a pathogen (e.g., a virus) inside the building. Displaying the current wellness index may include presenting the current wellness index on a client device of a user(s), while identifying the remediation action(s) may include instructing people to vacate the building, move to a specific portion of the building, use personal protective equipment inside the building, and/or clean one or more areas of the building.

For example, for the purpose of determining building occupancy (including occupancy on a floor-by-floor and/or room-by-room basis), building density, building foot traffic, tenant usage, and tenant engagement, the sensors 200 and data-collecting devices 300 may include threshold counters (e.g., at points of access and egress) for counting and recording the number of building occupants (and visitors) that have entered/exited the building, closed-circuit television (CCTV) for identifying discrete building occupants who have entered/exited the building, and/or individual access badges that may be scanned automatically or manually when the building occupant or visitor(s) enters/exits the building. In addition to, for example, predicting future occupancy, ascertaining foot traffic trends, and managing elevator queuing, such data may be used, inter alia, to ensure that the number of personnel within the building does not exceed government (e.g., health and safety) guidelines and/or protocols.

Such data may also be used to estimate optimal cleaning scheduling and staffing so that janitorial and cleaning staff operations may be adjusted. For example, under Use Caution, Moderate, and/or Good levels, janitorial and custodial staff may be used to continuously clean all high touch areas and high touch points, for example, in the building lobby and common areas. For the purpose of illustration rather than limitation, high touch points may include door handles, turnstiles, lobby desks, elevator buttons, sneeze guards, revolving doors, and the like. Furthermore, when conditions regarding public health and safety present an elevated risk (e.g., Use Caution level), janitorial and custodial personnel may be directed to perform additional cleaning, targeting paths of occupant travel and common areas in line with CDC guidelines. Sensors 200 and data-collecting devices 300 installed in building restrooms may also include push buttons by which users of the facilitates may indicate facility use, so that restocking of restroom supplies and periodic cleaning may be tailored to such use. Sensors 200 and data-collecting devices 300 may also be installed at other building amenity centers (e.g., snack bar, cafeteria, and so forth) to provide insight into amenity usage from which cleaning schedules may be optimized.

For the purpose of optimizing workspace needs and trends, sensors 200 and data-collecting devices 300 may include (e.g., floor and/or room) occupancy sensors by which insights into office assignment and meeting space needs and utilization, into employee space needs, into employee work habits, into team collaboration, into employee interaction, and the like may be gathered. Amenity occupancy sensors may also provide data for evaluating and optimizing amenity needs and utilization.

For the purpose of providing insight into building and/or occupant wellness and/or occupant comfort, the sensors 200 and data-collecting devices 300 may include (e.g., indoor and/or outdoor) air quality (AQ) sensors, (e.g., non-invasive) elevated body temperature sensors, and the like. AQ sensors may include humidity sensors, which may be used, inter alia, to maintain a humidity level within the building that may suppress pathogen transmission. For example, non-invasive, high-occupancy body temperature scanners may be installed in the building lobby and all occupants and visitors may be required to pass through. In addition to identifying individual occupants whose health may jeopardize that of other building occupants, such data may be used, for example, to determine when to replace and/or recalibrate AQ sensors, when to mitigate AQ events, and so forth. Social distancing badges may also be used to track contact between occupants.

In some implementations, a medical screening or care site and/or a medical testing lab may be included in the building. For example, in addition to wearing facial masks in accordance with CDC guidelines in all building common areas, visitors and occupants may be required to complete a (e.g., COVID-related) building access questionnaire before accessing the building. Building common areas may include, for the purpose of illustration rather than limitation, lobbies, elevators, stairwells, bathrooms, amenity centers, and so forth. Facial masks, protective gloves, hand sanitizer, and the like may also be provided at the medical screening or care site. In some instances, pathogen (e.g., COVID) testing may be performed and/or vaccinations may be provided.

In some implementations, occupants may be provided with a tenant engagement application ("app"). In some embodiments, the tenant engagement app is a mobile application used by occupants of the building to perform daily activities, including completion of a health attestation. The app also provides mechanisms to publish surveys to the occupants to get their feedback on conditions within the building, such as overall cleanliness. Data from the tenant engagement app, as well as health attestation, surveys, or other employee activity, may be used as inputs for the algorithm.

Public data sets may also be included in the logarithm. For the purpose of illustration rather than limitation, public data sets may include local hospitalization rates for flu-like symptoms, COVID cases in the region, and public mobility data to ascertain local crowding and density.

Sensors 200 and data-collecting devices 300 may also include sensors that, conventionally, are included with building systems for the purpose, for example, of monitoring some aspect of the building. Among these building system sensors 200 and data-collecting devices 300 are utility meters, water and air temperature sensors, furnace or boiler sensors, building work orders, and the like. Such data may provide insight into energy usage and energy cost optimization for the purpose of monitoring energy performance. Such data may also provide indicia of general building and/or building plant preventive maintenance needs that may be addressed prior to an emergency repair.

Figure 2:
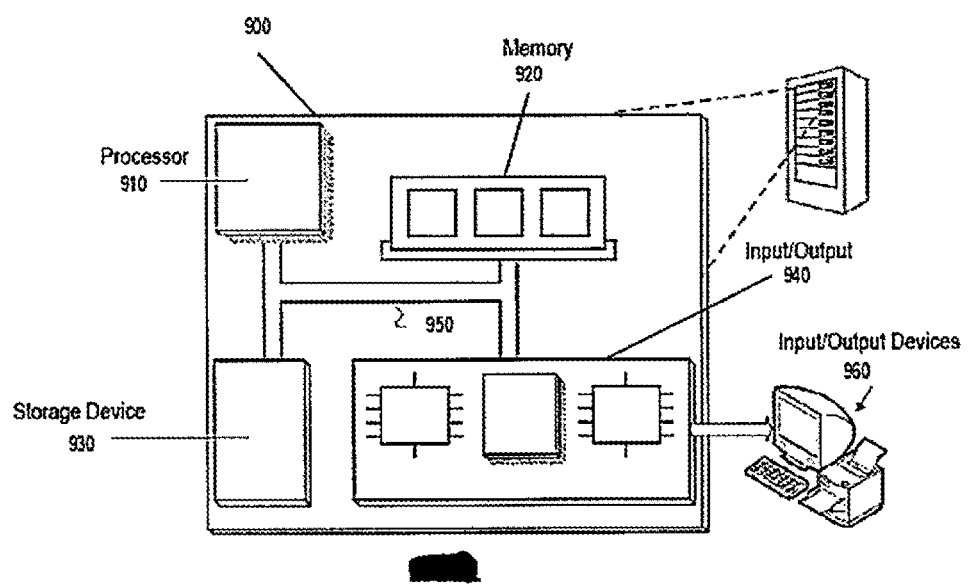
FIG. 2 shows a block diagram of an exemplary computer system for managing building wellness, in accordance with some embodiments of the present invention.

FIG. 2 shows a block diagram of an exemplary computer system 900 that may be used in implementing the technology described in this document. General-purpose computers, network appliances, mobile devices, or other electronic systems may also include at least portions of the system 900. In some implementations, the system 900 may include a processor 910, a memory 920, a storage device 930, and an input/output device 940. Each of the components 910, 920, 930, and 940 may be interconnected, for example, using a system bus 950.

Advantageously, the (e.g., single- or multi-threaded) processor 910 is capable of processing instructions for execution within the system 900. In some variations, these instructions may be stored in the memory 920 and/or on the storage device 930.

The memory 920 stores information within the system 900. In some implementations, the memory 920 may be a non-transitory computer-readable medium. In some implementations, the memory 920 may be a volatile memory unit. In some implementations, the memory 920 may be a non-volatile memory unit.

The storage device 930 is capable of providing mass (e.g., data) storage for the system 900. In some implementations, the storage device 930 may be a non-transitory computer-readable medium. In various different implementations, the storage device 930 may include, for example, a hard disk device, an optical disk device, a solid-date drive, a flash drive, or some other large capacity storage device. For example, the storage device may store long-term data (e.g., database data, file system data, etc.).

In some embodiments, the input/output device 940 provides input/output operations for the system 900. For example, in some implementations, the input/output device 940 may include one or more of: a network interface device, e.g., an Ethernet card; a serial communication device, e.g., an RS-232 port; and/or a wireless interface device, e.g., an 802.11 card, a 3G wireless modem, and/or a 4G wireless modem. In some implementations, the input/output device 940 may include driver devices configured to receive input data and to send output data to other input/output devices 960, e.g., keyboard, printer, and display devices. In some examples, mobile computing devices, mobile communication devices, and other devices may be used.

In some implementations, at least a portion of the approaches described above may be realized by instructions that, upon execution, cause one or more processing devices to carry out the processes and functions described above. Such instructions may include, for example, interpreted instructions such as script instructions, or executable code, or other instructions stored in a non-transitory computer readable medium. The storage device 930 may be implemented in a distributed way over a network, for example as a server farm or a set of widely distributed servers, or may be implemented in a single computing device.

Although an exemplary processing system 900 has been described in FIG. 1, embodiments of the subject matter, functional operations and processes described in this specification can be implemented in other types of digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible nonvolatile program carrier for execution by, or to control the operation of, data processing apparatus. Alternatively, or in addition, the program instructions can be encoded on an artificially generated propagated signal, e.g., a machine-generated electrical, optical, or electromagnetic signal that is generated to encode information for transmission to suitable receiver apparatus for execution by a data processing apparatus. The computer storage medium can be a machine-readable storage device, a machine-readable storage substrate, a random or serial access memory device, or a combination of one or more of them.

The term "system" may encompass all kinds of apparatuses, devices, and machines for processing data, including, for the purpose of illustration rather than limitation, a programmable processor, a computer, or multiple processors or computers. A processing system may include special purpose logic circuitry, e.g., an FPGA (field programmable gate array) or an ASIC (application specific integrated circuit). A processing system may include, in addition to hardware, code that creates an execution environment for the computer program in question, e.g., code that constitutes processor firmware, a protocol stack, a database management system, an operating system, or a combination of one or more of them.

A computer program (which may also be referred to or described as a program, software, a software application, an engine, a pipeline, a module, a software module, a script, or code) can be written in any form of programming language, including compiled or interpreted languages, or declarative or procedural languages, and it can be deployed in any form, including as a stand-alone program or as a module, component, sub-routine, or other unit suitable for use in a computing environment. A computer program may, but need not, correspond to a file in a file system. A program may be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program may also be deployed to be executed on a single computer or on multiple computers that, for example, are located at one site or distributed across multiple sites and interconnected by a communication network.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Computers suitable for the execution of a computer program can include, by way of example, general or special purpose microprocessors or both, or any other kind of central processing unit. Generally, a central processing unit will receive instructions and data from a read-only memory or a random access memory or both. A computer generally includes a central processing unit for performing or executing instructions and one or more memory devices for storing instructions and data. Generally, a computer will also include, or be operatively coupled to receive data from and/or transfer data to, one or more mass storage devices for storing data, e.g., magnetic, magneto-optical disks, or optical disks. However, a computer need not have such devices. Moreover, a computer may be embedded in another device, e.g., a mobile or cellular telephone, a personal digital assistant (PDA), a mobile audio or video player, a game console, a Global Positioning System (GPS) receiver, or a portable storage device (e.g., a universal serial bus (USB) flash drive), to name just a few.

Computer readable media suitable for storing computer program instructions and data include all forms of nonvolatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the subject matter described in this specification may be implemented on a computer having a display device, e.g., a CRT (cathode ray tube) or LCD (liquid crystal display) monitor, for displaying information to the user, as well as a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending Web pages to a Web browser on a user's user device in response to requests received from the Web browser.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

Although this specification contains many specific implementation details, these details should not be construed as limitations on the scope of what may be claimed, but rather as descriptions of features that may be specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous. Other steps or stages may be provided, or steps or stages may be eliminated, from the described processes. Accordingly, other implementations are within the scope of the following claims.

What is claimed is:

1. A method, implemented by a computer system associated with a building having one or more occupants, the method comprising the computer system:
   collecting, from a plurality of sensors disposed in and/or around the building and communicatively coupled with the computer system, data related to wellness of the building, the data comprising carbon monoxide levels, carbon dioxide levels, occupancy data, humidity data, particulate matter levels, ozone levels, volatile organic compound (VOC) levels, and formaldehyde levels;
   determining, based on aggregating the data and determining a plurality of risk levels for corresponding factors of a plurality of factors, a current wellness index for the building, the current wellness index providing an indication associated with a risk of being exposed to a pathogen inside the building, wherein:
      each risk level corresponds to a factor of the plurality of factors,
      the plurality of factors comprises carbon monoxide, carbon dioxide, occupancy in the building, humidity, particular matter, ozone, VOCs, and formaldehyde, and
      the determining the plurality of risk levels comprises determining a carbon monoxide risk level based on the collected carbon monoxide levels, determining a carbon dioxide risk level based on the collected carbon dioxide levels, determining an occupancy risk level based on the collected occupancy data, determining a humidity risk level based on the collected humidity data, determining a particulate matter risk level based on the collected particulate matter levels, determining an ozone risk level based on the collected ozone levels, determining a VOC risk level based on the collected VOC levels, and determining a formaldehyde risk level based on the collected formaldehyde levels; and
   identifying, based on the determined current wellness index, one or more remediation actions, and communicating the identified one or more remediation actions to a user of the computer system and/or to at least one of the one or more occupants.

2. The method of claim 1, wherein the building comprises an office building and the occupants comprise employees.

3. The method of claim 1, wherein the occupancy data comprises at least one of a number of occupants for the building or a population density for the building.

4. The method of claim 1, further comprising obtaining occupant wellness report data comprising data indicating one or more occupants is presently sick or recovering from recent illness.

5. The method of claim 1, wherein the current wellness index comprises water quality data comprises data describing water quality for a cooling tower.

6. The method of claim 1, wherein the current wellness index comprises building cleanliness data, the building cleanliness data including a length of time since a previous deep cleaning or a recent pathogen exposure.

7. The method of claim 1, further comprising obtaining historical building wellness index data comprising at least one of a rate of change for the wellness index or a trend for the wellness index.

8. The method of claim 1, wherein the pathogen comprises a virus.

9. The method of claim 1, further comprising sending a message comprising the current wellness index to at least one recipient, wherein the at least one recipient comprises an occupant from the one or more occupants.

10. The method of claim 1, further comprising displaying comprises, for the user, the determined current wellness index.

11. The method of claim 1, wherein identifying the one or more remediation actions comprises instructing people to do at least one of: vacate the building, move to a specific portion of the building, use personal protective equipment inside the building, or clean one or more areas of the building.

12. A system comprising:
   a computer system; and
   a plurality of sensors, communicatively coupled with the computer system, and disposed in and/or around a building having one or more occupants, the computer configured to perform operations comprising:
collecting, from the plurality of sensors, data related to wellness of the building, the data comprising carbon monoxide levels, carbon dioxide levels, occupancy data, humidity data, particulate matter levels, ozone levels, volatile organic compound (VOC) levels, and formaldehyde levels;
determining, based on aggregating the data and determining a plurality of risk levels for corresponding factors of a plurality of factors, a current wellness index for the building, the current wellness index providing an indication associated with a risk of being exposed to a pathogen inside the building, wherein:
each risk level corresponds to a factor of the plurality of factors,
the plurality of factors comprises carbon monoxide, carbon dioxide, occupancy in the building, humidity, particular matter, ozone, VOCs, and formaldehyde, and
the determining the plurality of risk levels comprises determining a carbon monoxide risk level based on the collected carbon monoxide levels, determining a carbon dioxide risk level based on the collected carbon dioxide levels, determining an occupancy risk level based on the collected occupancy data, determining a humidity risk level based on the collected humidity data, determining a particulate matter risk level based on the collected particulate matter levels, determining an ozone risk level based on the collected ozone levels, determining a VOC risk level based on the collected VOC levels, and determining a formaldehyde risk level based on the collected formaldehyde levels; and
identifying, based on the determined current wellness index identifying one or more remediation actions and communicating the identified one or more remediation actions to a user of the computer system and/or to at least one of the one or more occupants.

13. The system of claim 12, wherein the building comprises an office building and the occupants comprise employees.

14. The system of claim 12, wherein the occupancy data comprises at least one of a number of occupants for the building or a population density for the building.

15. The system of claim 12, further comprising obtaining occupant wellness report data comprising data indicating one or more occupants is presently sick or recovering from recent illness.

16. The system of claim 12, wherein the current wellness index comprises water quality data describing water quality for a cooling tower.

17. The system of claim 12, wherein the current wellness index comprises building cleanliness data, the building cleanliness data including a length of time since a previous deep cleaning or a recent pathogen exposure.

18. The system of claim 12, further comprising obtaining historical building wellness index data comprising at least one of a rate of change for the wellness index or a trend for the wellness index.

19. The system of claim 12, wherein the pathogen comprises a virus.

20. The system of claim 12, further comprising sending a message comprising the current wellness index to at least one recipient, wherein the at least one recipient comprises an occupant from the one or more occupants.

21. The system of claim 12, further comprising displaying presenting, for the user, the determined current wellness index.

22. The system of claim 12, wherein identifying the one or more remediation actions comprises instructing people to do at least one of: vacate the building, move to a specific portion of the building, use personal protective equipment inside the building, or clean one or more areas of the building.

23. A non-transitory computer-readable medium having instructions stored thereon that, when executed by a computer system associated with a building having one or more occupants, cause the computer system to perform operations comprising:
collecting, from a plurality of sensors disposed in and/or around the building and communicatively coupled with the computer system, a data related to wellness of the building, the data comprising carbon monoxide levels, carbon dioxide levels, occupancy data, humidity data, particulate matter levels, ozone levels, volatile organic compound (VOC) levels, and formaldehyde levels;
determining, based on aggregating the data and determining a plurality of risk levels for corresponding factors of a plurality of factors, a current wellness index for the building, the current wellness index providing an indication associated with a risk of being exposed to a pathogen inside the building, wherein:
each risk level corresponds to a factor of the plurality of factors,
the plurality of factors comprises carbon monoxide, carbon dioxide, occupancy in the building, humidity, particular matter, ozone, VOCs, and formaldehyde, and
the determining the plurality of risk levels comprises determining a carbon monoxide risk level based on the collected carbon monoxide levels, determining a carbon dioxide risk level based on the collected carbon dioxide levels, determining an occupancy risk level based on the collected occupancy data, determining a humidity risk level based on the collected humidity data, determining a particulate matter risk level based on the collected particulate matter levels, determining an ozone risk level based on the collected ozone levels, determining a VOC risk level based on the collected VOC levels, and determining a formaldehyde risk level based on the collected formaldehyde levels; and
identifying, based on the determined current wellness index identifying one or more remediation actions, and communicating the identified one or more remediation actions to a user of the computer system and/or to at least one of the one or more occupants.

* * * * *